(12) United States Patent
Miyazaki et al.

(10) Patent No.: US 7,588,944 B2
(45) Date of Patent: Sep. 15, 2009

(54) METHOD OF ANALYZING C-TERMINAL AMINO ACID SEQUENCE OF PEPTIDE

(75) Inventors: Kenji Miyazaki, Tokyo (JP); Akira Tsugita, Tokyo (JP); Kenichi Kamijo, Tokyo (JP)

(73) Assignee: NEC Corporation, Tokyo (JP)

( * ) Notice: Subject to any disclaimer, the term of this patent is extended or adjusted under 35 U.S.C. 154(b) by 265 days.

(21) Appl. No.: 10/589,495

(22) PCT Filed: Aug. 24, 2004

(86) PCT No.: PCT/JP2004/012107

§ 371 (c)(1),
(2), (4) Date: Aug. 15, 2006

(87) PCT Pub. No.: WO2005/078447

PCT Pub. Date: Aug. 25, 2005

(65) Prior Publication Data

US 2008/0213911 A1    Sep. 4, 2008

(30) Foreign Application Priority Data

Feb. 17, 2004    (JP) ............... 2004-039885

(51) Int. Cl.
*G01N 33/00* (2006.01)
(52) U.S. Cl. .......... 436/89; 436/173; 250/288; 250/281; 250/282; 250/283; 435/23
(58) Field of Classification Search .............. None
See application file for complete search history.

(56) References Cited

U.S. PATENT DOCUMENTS

| | | | | |
|---|---|---|---|---|
| 3,836,433 A | * | 9/1974 | Wirth et al. .......... | 435/181 |
| 5,442,106 A | * | 8/1995 | Zeldin et al. .......... | 562/512 |
| 5,952,653 A | * | 9/1999 | Covey et al. .......... | 250/288 |

FOREIGN PATENT DOCUMENTS

| | | |
|---|---|---|
| JP | 10-293130 A | 11/1998 |
| JP | 2003-279581 A | 10/2003 |

OTHER PUBLICATIONS

Tsgita, Akira, et al., Additoinal possible tools for identification of protein on one- or two-dimentioanal electrophoesis, 1998, Electrophoresis, vol. 19, p. 928-938.*

Vogt, S., et al., Effective esterification of carboxymethyl cellulose in a new non-aqueous swelling system, 1996, Polymer Bulletin, vol. 36, p. 549-555.*

Kenji Miyazaki et al. "C-Terminal Sequencing Method for Proteins in Gel by The Reaction of Acetic Anhydride with Perfluoric Acid", Seikagaku vol. 75, No. 8, p. 924, (2003).

David H. Hawke et al. "Microsequence Analysis of Peptides and Proteins: Trimethylsilylisothiocyanate as a Reagent for COOH-Terminal Sequence Analysis" Analytical Biochemistry, 166, pp. 298 to 307, (1987).

Akira Tsugita et al. "C-Terminal Sequencing of Protein, A Novel Partial Acid Hydrolysis and Analysis by Mass Spectrometry" Research Institute for Biosciences, Science University of Tokyo, Jan. 23, 1992, pp. 43 to 48.

(Continued)

*Primary Examiner*—Yelena G Gakh
*Assistant Examiner*—Robert Xu
(74) *Attorney, Agent, or Firm*—Sughrue Mion, PLLC

(57) ABSTRACT

An analyte peptide is selectively degraded sequentially by using an alkanoic anhydride (S101). The original peptide and a series of degradation reaction products having peptide in which one or more C-terminal-sided amino acids are deleted, are subjected to a certain posttreatment (S102). The molecular weight of the reaction products is measured by mass spectrometry (S103). And, the amino acid sequence of the original peptide from C-terminal is determined, based on the molecular weight obtained by mass spectrometry (S104).

22 Claims, 13 Drawing Sheets

OTHER PUBLICATIONS

Akira Tsugita et al. "Reaction of Pentafluoropropionic Anhydride Vapor on Polypeptide as Revealed by Mass Spectrometry. A Carboxypeptidase Mimetic Degradation", The Chemical Society of Japan, Chemistry letters, pp. 235-238, 1992.

Keiji Takamoto et al. "Carboxy-Terminal Degradation of Peptides using Perfluoroacyl Anhydrides A C-Terminal Sequencing Method" Research Institute for Biosciences, Department of Pharmacology, Science University of Tokyo, Japan, pp. 228, 362-372, (1995).

* cited by examiner

FIG. 5

REACTION CONDITION OF ACETYLATION AND TRUNCATION OF PROTEIN IN GEL
(WITHOUT USE OF PERFLUORIC ACID)

| REACTION | REAGENT COMPOSITION | TEMPERATURE | PERIOD |
|---|---|---|---|
| ACETYLATION AND TRUNCATION | 1%~30% $Ac_2O$/FoA | 50~100°C | 4 TO 110 HOURS |

REACTION CONDITION OF HYDROLYSIS OF PROTEIN IN GEL

| REACTION | REAGENT COMPOSITION | TEMPERATURE | PERIOD |
|---|---|---|---|
| HYDROLYSIS | 10~20% AQUEOUS DMAE SOLUTION | 50~70°C | 30 TO 120 MINUTES |

FIG. 7 myoglobin-horse

[1-153] mass = 17738.180
Cleavage at R

| | | | | | |
|---|---|---|---|---|---|
| Small polar: | D(7) | E(13) | N(3) | Q(6) | |
| Large polar: | K(19) | R(2) | H(11) | | |
| Small non-polar: | S(5) | T(7) | A(15) | G(15) | |
| Large non-polar: | L(17) | I(9) | V(7) | M(2) | F(7) | Y(2) | W(2) |
| Special: | C(0) | P(4) | | | |

K[16] + 42.04   K[42] + 42.04   K[45] + 42.04   K[47] + 42.04
K[50] + 42.04   K[56] + 42.04   K[62] + 42.04   K[63] + 42.04
K[77] + 42.04   K[78] + 42.04   K[79] + 42.04   K[87] + 42.04
K[96] + 42.04   K[98] + 42.04   K[102] + 42.04  K[118] + 42.04
K[133] + 42.04  K[145] + 42.04  K[147] + 42.04

```
1    G L S D G E W Q Q V L N V W G K V E A D I A G H G Q E V L I    30
31   R l f t g h p e t l e k f d k f k h l k t e a e m k a s e d    60
61   l k k h g t v v l t a l g g i l k k k g h h e a e l k p l a    90
91   q s h a t k h k i p i k y l e f i s d a i i h v l h s k h p    120
121  g n f g a d a q g a m t k a l e l f r N D I A A K Y K E L G    150
151  F Q G                                                          153
```

(1)   [1-31] = 3444.742   (2)   [32-139] = 12692.649   (3)   [140-153] = 1636.809

METHOD OF ANALYZING C-TERMINAL AMINO ACID SEQUENCE OF PEPTIDE

This application claims priority from PCT Application No. PCT/JP2004/012107 filed Aug. 24, 2004, and from Japanese Patent Application No. 2004-039885 filed Feb. 17, 2004, which applications are incorporated herein by reference.

TECHNICAL FIELD

The present invention relates to a method of analyzing the C-terminal amino acid sequence of the peptide.

BACKGROUND ART

Information on the amino acid sequence of naturally obtained peptides and proteins is essential in studies on the biological properties and functions thereof. Currently, all amino acid sequences of peptides and proteins are determined from the corresponding genetic information, namely, estimated on the basis of sequence of the genomic genes or c-DNAs prepared from m-RNAs coding these peptides. The amino acid sequence of proteins is also determined directly by various methods, alternatively. Information on partial amino acid sequence of a peptide is nevertheless needed in specifying a genomic gene or a c-DNA prepared from m-RNA coding the peptide.

Information on N- and C-terminal amino acid sequences of peptide is considered particularly useful as the information on the partial amino acid sequence of the peptide. For example if N-terminal amino acid sequence and C-terminal amino acid sequence are available, in selecting a c-DNA coding an analyte peptide from a c-DNA library prepared from a number of m-RNAs, it becomes possible to prepare a nucleic acid probe based on the amino acid sequences at both terminals and select a desirable c-DNA by using the probe obtained. It is also possible to amplify a desirable c-DNA selectively by applying the Polymerase Chain Reaction (PCR) method, by using the oligonucleotide primer prepared based on the amino acid sequences at both terminals.

A method of degrading N-terminal amino acids sequentially by using Edman degradation and identifying the amino acid derivatives produced has been conventionally used in analyzing the N-terminal amino acid sequence of a peptide.

On the other hand, methods of sequentially degrading C-terminal amino acids chemically and specifying the degraded C-terminal amino acids from the difference in molecular weight between shortened peptides obtained as the reaction products, and the original peptide has been proposed as a means which analyzes the C-terminal amino acid sequence of the peptide (see, Non-Patent Documents 1, 2, and 3).

Non-Patent Document 1 discloses a method of degrading C-terminal amino acids sequentially by a chemical method. It is a method of accelerating selective hydrolysis of C-terminal amino acids by heating a dry peptide to 90° C. and allowing a vapor from a high-concentration aqueous solution of pentafluoropropanoic acid ($CF_3CF_2COOH$) or heptafluorobutanoic acid ($CF_3CF_2CF_2COOH$) to act on the peptide.

Alternatively, Non-Patent Documents 2 and 3 disclose methods of degrading C-terminal amino acids selectively by using an acetonitrile solution of pentafluoropropanoic anhydride (($CF_3CF_2CO)_2O$) or heptafluorobutanoic anhydride (($CF_3CF_2CF_2CO)_2O$) instead of the high-concentration aqueous solution of perfluoroalkanoic acid. It is reported that generation of the side reactions could be avoided, for example, by allowing the vapor of the solution to act on a dry peptide while cooling the solution to −18° C. and thus, preventing penetration of the water molecules vaporized from the solution into the system.

In these conventional C-terminal degradation methods, an oxazolone ring structure is seemingly formed as a reaction intermediate from the C-terminal amino acid in the dehydration reaction represented by the reaction formula (I) below. The reaction represented by the reaction formula (II) below occurs then in reaction of perfluoroalkanoic acid with the oxazolone ring. As a result of this, it is reported that the C-terminal amino acid is achieved to be degraded selectively.

The selective degradation reaction of C-terminal amino acids proceeds sequentially, giving a mixture containing a series of reaction products in which one to ten or more amino acid residues have been deleted from the C-terminal of the original peptide when a predetermined processing period. When the mass of the ionic species derived from respective reaction products is measured by analyzing the mixture containing a series of reaction products by mass spectrometry, a series of peaks showing the difference in mass reflecting the C-terminal amino acid sequence are measured.

For example, each of reaction products generated by sequential degradation reaction of C-terminal amino acid from the original peptide is a group of a series of reaction products of several types, up to reaction products in which several amino acid residues have been deleted from the original peptide. It is possible to analyze the mass of the corresponding ionic species all together by subjecting the reaction products to analysis by mass spectrometry. It is considered possible to determine the C-terminal amino acid sequence over several amino acid residues collectively from the mass of the ionic species corresponding to the deleted C-terminal-sided amino acids.

[Formula 1]

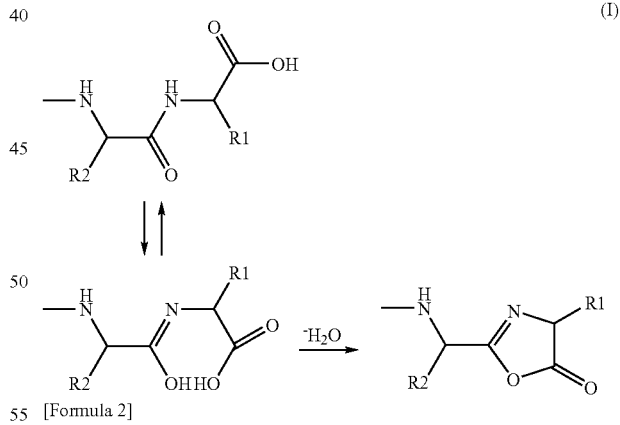

[Formula 2]

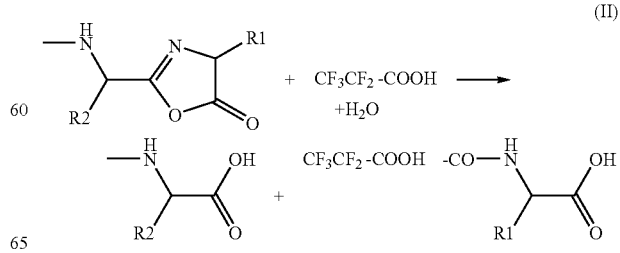

Non-Patent Document 1: Tsugita, A. et al., Eur. J. Biochem., 1992, 206, p. 691-696

Non-Patent Document 2: Tsugita, A. et al., Chem. Lett., 1992, p. 235-238

Non-Patent Document 3: Takamoto, K. et al., Eur. J. Biochem. 228, 1995, p. 362-372

DISCLOSURE OF THE INVENTION

The conventional method of supplying the vapor of a perfluoroalkanoic acid or perfluoroalkanoic anhydride and allowing them to react with a dry peptide in gas phase is considered to be a useful method of analyzing C-terminal amino acid sequences. However, the present inventors have found in analysis by using the method that it still has rooms to be improved in generality.

After intensive studies on the reasons, the present inventors have found that the perfluoroalkanoic acid or perfluoroalkanoic anhydride used in the sequential peptide C-terminal degradation occasionally lead to side reactions because the reactivity thereof to the peptide is relatively high.

For example in the method disclosed in Non-Patent Document 1, N and O-acyl transfer reactions between the α-amino group (—NH—) and the β-hydroxyl group (—OH) and the subsequently hydrolysis might proceed on the serine residues (—NH—CH(CH$_2$OH)—CO—) in peptide. The proceeding of the hydrolysis leads to cleavage of the peptide at the N-terminal side of the serine residue as a side reaction. Hydrolysis in a similar mechanism may occur also on the threonine residues (—NH—CH(CH(CH$_3$)OH)—CO—) having a β-hydroxyl group, leading to cleavage of the peptide at the N-terminal side of the threonine residues.

In addition, transfer of a peptide bond from the C-terminal carboxyl group to a β-carboxyl group and subsequent hydrolysis may proceed on the aspartic acid residues (—NH—CH(CH$_2$COOH)—CO—) in the peptide, leading to cleavage of the peptide at the C-terminal side of the aspartic acid residue.

When a long peptide chain is cleaved in these side reactions, sequential degradation of C-terminal amino acids of the N-terminal-sided peptide fragments are also proceeded at the same time. Presence of the reaction products due to these side reactions may lead to inhibition of the analysis of desirable reaction products by mass spectrometry in some cases.

Even if it does not result in cleavage of the peptide, an amide bond is lost in the region when a partial N-terminal-sided peptide is transferred onto a β-hydroxyl group to be a branched peptide. The oxazolone ring structure represented by Formula (I) above is thus not formed, and the selective degradation reaction of the C-terminal amino acid does not proceed any more.

On the other hand, the method disclosed in Non-Patent Document 2 or 3 had an advantage that it is possible to avoid generation of such side reactions effectively, because the system contains no water molecule that vaporizes from solution. However, the perfluoroalkanoic anhydride used is high reactive and, for prevention of the side reactions, the processing temperature should be kept at a low temperature, for example at −18° C. for prevention of dew formation. Thus, there has been a room for improvement for simplifying the operations of sequential C-terminal degradation.

An object of the present invention, which was made in view of the circumstances above, is to provide a technique of degrading C-terminal amino acids of a peptide sequentially under mild condition. An other object of the present invention is to provide a general technique of analyzing C-terminal amino acids of a peptide reliably.

According to the present invention, there is provided a method of analyzing a C-terminal amino acid sequence of a peptide, including obtaining C-terminal-deleted peptides lacking amino acid residues from the C-terminal by degrading the amino acids from the peptide C-terminal sequentially, measuring the molecular weight of the C-terminal-deleted peptides, and determining the decrease in molecular weight associated with the sequential degradation from the difference between the molecular weight obtained in the measuring the molecular weight of the C-terminal-deleted peptides and the molecular weight of the peptide, and analyzing the C-terminal amino acid sequence based on the decrease in molecular weight, wherein the C-terminal amino acids are degraded by making the peptide substantially bring into contact with an alkanoic anhydride in the obtaining C-terminal-deleted peptides.

In the method according to the present invention, the peptide is sequentially degraded substantially by using an alkanoic anhydride. Thus, it is possible to obtain C-terminal-deleted peptides in which the amino acid residues are degraded sequentially from the C-terminal, for example, from a peptide containing a number of amino acid residues such as protein, by sequentially degrading the C-terminal amino acids of the peptide chemically under a mild condition containing substantially no perfluoroalkanoic acid or the like. It is thus possible to analyze the C-terminal amino acid sequence based on the decrease in molecular weight due to sequential deletion of a series of amino acids, while suppressing the side reactions during the sequential degradation. It is also possible to analyze the C-terminal amino acid sequence of the peptide reliably and in more general way, because the C-terminal amino acid sequence is analyzed based on the decrease in molecular weight.

In the present invention, the alkanoic anhydride to be brought into contact with the peptide may be a substituted or unsubstituted alkanoic anhydride, but not a perfluoroalkanoic acid or the anhydride thereof. When a substituted alkanoic anhydride is used, an alkanoic anhydride substituted with atoms other than halogen atoms is preferably used.

The method of analyzing the C-terminal amino acid sequence of the peptide according to the present invention includes the measuring the molecular weight of the peptide, wherein the analyzing the amino acid sequence enables the decrease in molecular weight associated with the sequential degradation to be determined from the difference between the molecular weight obtained in the measuring the molecular weight of C-terminal-deleted peptides and the molecular weight obtained in the measuring the molecular weight of the peptide. In this way, it is reliably possible to determine the kinds of the amino acid residues deleted from the C-terminal based on the difference in molecular weight. It is thus possible to analyze the C-terminal amino acid sequence of the peptide further more reliably.

The method of analyzing the C-terminal amino acid sequence of the peptide according to the present invention may include allowing water molecules to act on the C-terminal-deleted peptides after the obtaining the C-terminal-deleted peptides and before the measuring the molecular weight of the C-terminal-deleted peptides. In this way, it is possible to form a carboxyl group reliably on the C-terminal of the C-terminal-deleted peptides sequentially degraded.

In the method of analyzing the C-terminal amino acid sequence of the peptide according to the present invention, the allowing water molecules to act may include bringing the C-terminal-deleted peptides into contact with an aqueous solution containing a basic nitrogen-containing compound or a tertiary amine. In this way, it is possible to perform the hydrolysis reaction more reliably in the allowing water molecules to react.

By the sequential degradation reaction of C-terminal amino acid according to the present invention, it is possible to prepare a processed sample containing a series of reaction products deleting, for example, up to 10 amino acid residues. The information on C-terminal amino acid sequence used in preparation of a nucleic acid probe or primer may usually contain information on a base sequence, for example, of approximately 18 to 24 base lengths coding an amino acid sequence, that is, on an amino acid sequence of approximately 6 to 8-aminoacids. Thus, the method according to the present invention is used favorably in these applications.

On the other hand, when the analyte peptide is a peptide containing many amino acid residues such as protein, the molecular weight range weight of the peptide itself may be greater than the molecular of the sample favorable for mass spectrometric measurement. It is occasionally not possible to obtain sufficient measurement accuracy, because the change in formula weight when an amino acid residues is deleted from the C-terminal is relatively smaller with respect to the molecular weight of the peptide.

Thus in the present invention, during analysis of the C-terminal amino acid sequence of the peptide having a large molecular weight such as protein, the peptide may be processed by the procedure below including selectively cleaving the peptide.

According to the present invention, there is also provided a method of analyzing the C-terminal amino acid sequence of the peptide, including obtaining C-terminal-deleted peptides lacking amino acid residues from the C-terminal by degrading the amino acids from the C-terminal of the peptide sequentially, obtaining C-terminal-deleted peptide-derived peptide fragments by cleaving the C-terminal-deleted peptides at predetermined positions, measuring the molecular weight of the C-terminal-deleted peptide-derived peptide fragments, determining the decrease in molecular weight associated with the sequential degradation from the difference between the molecular weight obtained in the measuring the molecular weight of C-terminal-deleted peptide-derived peptide fragments and the molecular weight of the peptide fragments obtain able from the peptide and analyzing the C-terminal amino acid sequence based on the decrease in molecular weight, wherein the C-terminal amino acids are degraded while the peptide is substantially brought into contact with an alkanoic anhydride in the obtaining C-terminal-deleted peptides.

In the method according to the present invention, after the sequential degradation reaction of C-terminal amino acid, the mixture containing a series of reaction products in which predetermined numbers of amino acid residues in the original peptide are respectively deleted from the C-terminal is subjected to selective peptide-chain cleavage at a particular amino acid position. The long peptide chain may be digested then with an enzyme, for example, a obtained protease such as trypsin, having a cleavage site specificity. The peptide fragments are then analyzed by mass spectrometry.

Thus, the mixture of the peptide fragments obtained by enzyme digestion contains the C-terminal-sided peptide fragments derived from original peptide and the C-terminal-sided peptide fragments derived from a series of reaction products in which predetermined numbers of amino acid residues are respectively deleted from the C-terminal. It is possible to measure a series of peaks showing the difference in mass reflecting the C-terminal amino acid sequence at a sufficient molecular-weight resolution, by measuring the mass of the ionic species corresponding to each C-terminal-sided peptide fragment derived from each reaction product, while analyzing the C-terminal-sided peptide fragments derived from the original peptide and the series of reaction products by mass spectrometry.

The method of analyzing the C-terminal amino acid sequence of the peptide according to the present invention may include obtaining peptide-derived peptide fragments by cleaving the peptide at the predetermined positions above and measuring the molecular weight of the peptide-derived peptide fragments; and, in the analyzing the amino acid sequence, the decrease in molecular weight associated with the sequential degradation may be determined from the difference between the molecular weight obtained in the measuring the molecular weight of the peptide-derived peptide fragments and the molecular weight obtained in the measuring the molecular weight of C-terminal-deleted peptide-derived peptide fragments. In this way, it is possible to analyze the kinds of amino acid residues deleted from the peptide C-terminal, by comparing the difference in molecular weight with the molecular weight of amino acids.

The method of analyzing the C-terminal amino acid sequence of the peptide according to the present invention may include protecting particular amino acid residues in the peptide before the obtaining the C-terminal-deleted peptides and thus eliminating the susceptibility of the particular amino acid residues to cleavage in the obtaining the C-terminal-deleted peptide-derived peptide fragments. In this way, it is possible to improve the site selectivity of the peptide fragmentation.

In the method of analyzing the C-terminal amino acid sequence of the peptide according to the present invention, the obtaining the C-terminal-deleted peptide-derived peptide fragments may include treating the C-terminal-deleted peptides with a protease. It is thus possible to cleave the peptide at predetermined positions selectively.

In the method of analyzing the C-terminal amino acid sequence of the peptide according to the present invention, the protease may be trypsin, and the eliminating the susceptibility of the particular amino acid residues may contain N-acylating the peptide. In this way, it is possible to cleave the peptide at the C-terminal sides of arginine residues and obtain the fragment peptides stably.

In the method of analyzing the C-terminal amino acid sequence of the peptide according to the present invention, the protection may be O- and N-acylation of the peptide, and the protecting groups by O-acylation may be deprotected after the obtaining the C-terminal-deleted peptide fragments and before the obtaining the C-terminal-deleted peptide-derived peptide fragments. In this way, it is possible to analyze the amino acid sequence further more accurately in the analyzing C-terminal amino acid sequence.

If the form in which the molecular weight of the C-terminal-sided peptide fragments obtained is measured after selective cleavage reaction of C-terminal amino acids and additional enzyme digestion by using a protease having cleavage-site specificity, N-terminal-sided peptide fragments inevitably produced by the enzyme digestion are also observed on the mass spectrum at the same time.

It is thus possible to improve the generality further more, by using a method of differentiating the peaks derived from the C-terminal-sided peptides fragments derived from the original peptide and a series of reaction products from the peaks derived from N-terminal-sided peptide fragments other than those at high accuracy and determining the molecular weight of each of the peaks derived from the C-terminal-sided peptide fragments derived from the desirable original peptide and a series of reaction products at higher accuracy.

In the present invention, it is possible to identify the C-terminal-sided peptide fragments and the peptide fragments of the C-terminal amino acid-deleted peptides easily in the configuration below.

In the method of analyzing the C-terminal amino acid sequence of the peptide according to the present invention, the measuring the molecular weight of C-terminal-deleted peptide-derived peptide fragments may contain performing mass spectrometric measurement based on cationic and anionic species, and the analyzing the amino acid sequence from the C-terminal may include identifying the C-terminal-deleted peptide-derived peptide fragments associated with the C-terminal of the peptide by comparing the mass spectrometric results based on cationic and the mass spectrometric results based on anionic species. In this way, it is possible to identify the C-terminal-deleted peptide-derived peptide fragments and the peptide-derived peptide fragments more easily and determine the molecular weight thereof during analysis of the peptide amino acid sequence. It is thus possible to perform the analysis of amino acid sequence more reliably.

The method of analyzing the C-terminal amino acid sequence of the peptide according to the present invention may include allowing water molecules to act on the C-terminal-deleted peptides after the obtaining the C-terminal-deleted peptides and before the obtaining the C-terminal-deleted peptide-derived peptide fragments. In this way, it is possible to form a carboxyl group on the C-terminal of the sequentially degraded C-terminal-deleted peptides reliably. It is thus possible to improve the accuracy and reliability of the analysis.

In the method of analyzing the C-terminal amino acid sequence of the peptide according to the present invention, the allowing water molecules to act may include bringing the C-terminal-deleted peptides into contact with an aqueous solution containing a basic nitrogen-containing aromatic ring compound or a tertiary amine. In this way, it is possible to perform the hydrolysis reaction in the allowing water molecules to react more reliably.

In the method of analyzing the C-terminal amino acid sequence of the peptide according to the present invention, the obtaining the C-terminal-deleted peptides may be performed while the peptide is retained in the gel. In this way, it is possible to obtain C-terminal-deleted peptides of a peptide retained in gel for example by gel electrophoresis more easily.

In the method of analyzing the C-terminal amino acid sequence of the peptide according to the present invention, the processings prior to the measuring the molecular weight of C-terminal-deleted peptide may be performed in the gel. Also in the method of analyzing the C-terminal amino acid sequence of the peptide according to the present invention, the processing prior to the measuring the C-terminal-deleted peptides-derived peptide fragments is performed in the gel. In this way, it is possible to prepare a sample for molecular weight measurement stably in simple operation.

The method of analyzing the C-terminal amino acid sequence of the peptide according to the present invention may include crosslinking the peptide before the obtaining the C-terminal-deleted peptides. In this way, it is possible to improve the accuracy and reliability of analysis more.

The method of analyzing the C-terminal amino acid sequence of the peptide according to the present invention may include isolating the peptide from the peptide-containing mixture by polyacrylamide gel electrophoresis before the obtaining the C-terminal-deleted peptides, and the obtaining the C-terminal-deleted peptides may be performed while the isolated peptide is retained in the gel used in the polyacrylamide gel electrophoresis.

In the method of analyzing the C-terminal amino acid sequence of the peptide according to the present invention, the obtaining the C-terminal-deleted peptides may include immersing the gel in a solution of an alkanoic anhydride in a dipolar aprotic solvent. In this way, it is possible to perform sequential degradation of C-terminal amino acid of the peptide under mild condition reliably.

In the method of analyzing the C-terminal amino acid sequence of the peptide according to the present invention, the obtaining the C-terminal-deleted peptides may be performed in a system containing a basic nitrogen-containing aromatic ring compound. In this way, it is possible to improve the reaction rate of the sequential degradation reaction of C-terminal amino acids. It is thus possible to provide a more general method of analyzing the C-terminal amino acid sequence under mild condition.

In the method of analyzing the C-terminal amino acid sequence of the peptide according to the present invention, the basic nitrogen-containing aromatic ring compound may be a pyridine base or the derivative thereof. In this way, it is possible to increase the reaction rate of the sequential degradation of C-terminal amino acid more reliably.

In the method of analyzing the C-terminal amino acid sequence of the peptide according to the present invention, the alkanoic anhydride may be the symmetric anhydride of an alkanoic acid of 2 or more and 6 or less carbon atoms. Alternatively in the method of analyzing the C-terminal amino acid sequence of the peptide according to the present invention, the alkanoic anhydride may be the symmetric anhydride of a straight-chain alkanoic acid of 2 or more and 6 or less carbon atoms. In this way, it is possible to perform the sequential degradation of C-terminal amino acid reliably.

Combinations of the configurations above and modifications in representation of method and device of the present invention are also included in the favorable embodiments of the present invention.

For example in the present invention, the measuring the molecular weight of C-terminal-deleted peptides may include immersing the peptide retained in the gel in a solution of the alkanoic anhydride in a dipolar aprotic solvent. In this way, it is possible to advance acylation of an amino group and a hydroxyl group in the peptide and sequential degradation of the C-terminal amino acids reliably. It is thus possible to perform the selective sequential degradation reaction under mild condition stably.

As described above, according to the present invention, a technique of degrading the C-terminal amino acids of the peptide sequentially under mild condition is realized by using a reaction reagent substantially containing an alkanoic anhydride. The present invention also provides a technique higher in generality of analyzing the C-terminal amino acids of the peptide reliably.

BRIEF DESCRIPTION OF THE DRAWINGS

The objects described above, other objects, the characteristics and advantages of the invention will be more apparent with reference to the favorable embodiments described below and the following drawings associated therewith:

FIG. 5 includes charts showing the reaction conditions in analysis of the C-terminal amino acid sequence of the peptide according to the embodiment;

FIG. 7 is a Table showing the amino acid sequence of the globin peptide chain in horse myoglobin;

DESCRIPTION OF THE PREFERRED EMBODIMENTS

Hereinafter, embodiments of the present invention will be described with reference to drawings.

Figure 1:
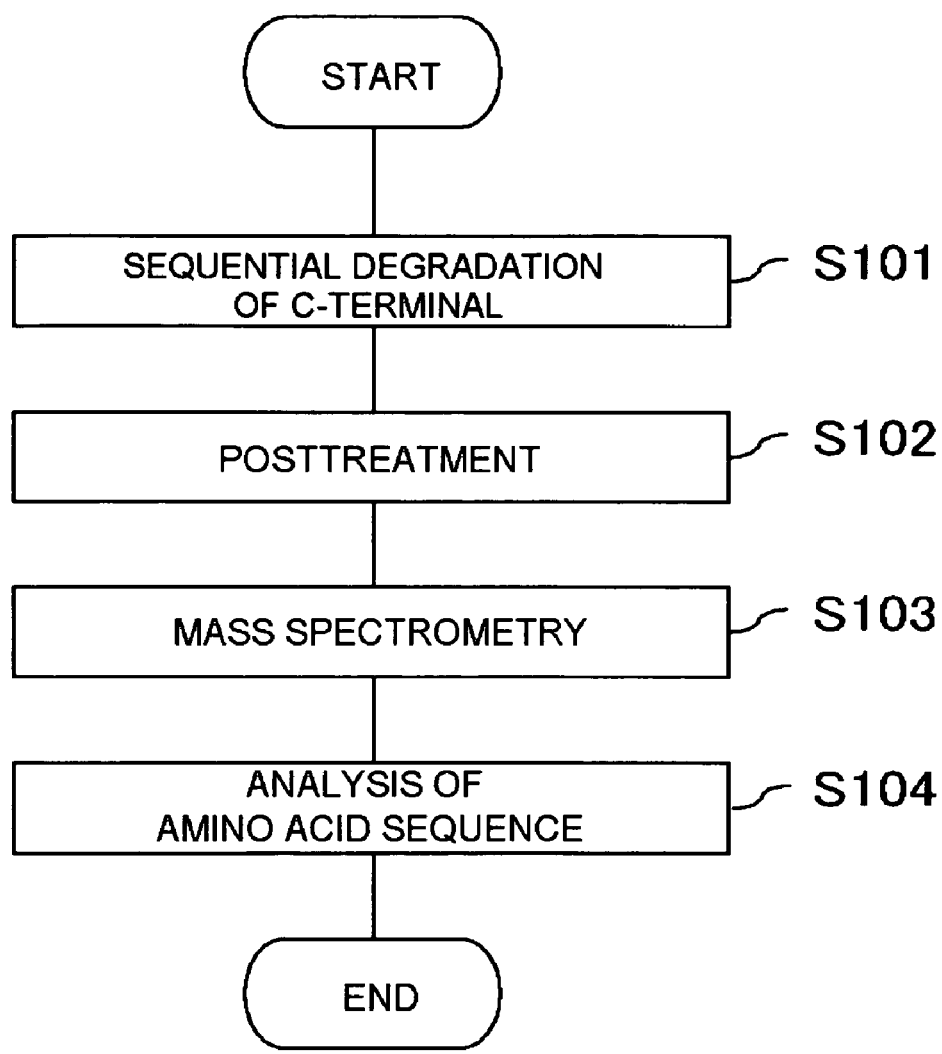
FIG. 1 is a flow chart showing the procedure of analyzing the C-terminal amino acid sequence of the peptide according to the embodiment.

FIG. 1 is a flowchart showing the procedure of analyzing C-terminal amino acids of a peptide in the present embodiment.

In FIG. 1, C-terminal amino acids of an analyte peptide is first degraded sequentially (S101). The degradation gives a series of degradation reaction products including the original peptide and peptides lacking one or more C-terminal-sided amino acids. The reaction products are then subjected to a particular posttreatment (S102). The molecular weight of the reaction products is then measured by mass spectrometry (S103). The amino acid sequence of the original peptide from C-terminal is determined, based on the molecular weight obtained by the mass spectrometry (S104).

Thus, the procedure shown in FIG. 1 consists of three basic steps 101, 103, and 104 in the present embodiment and a step 102 between the steps 101 and 103.

Figure 2:
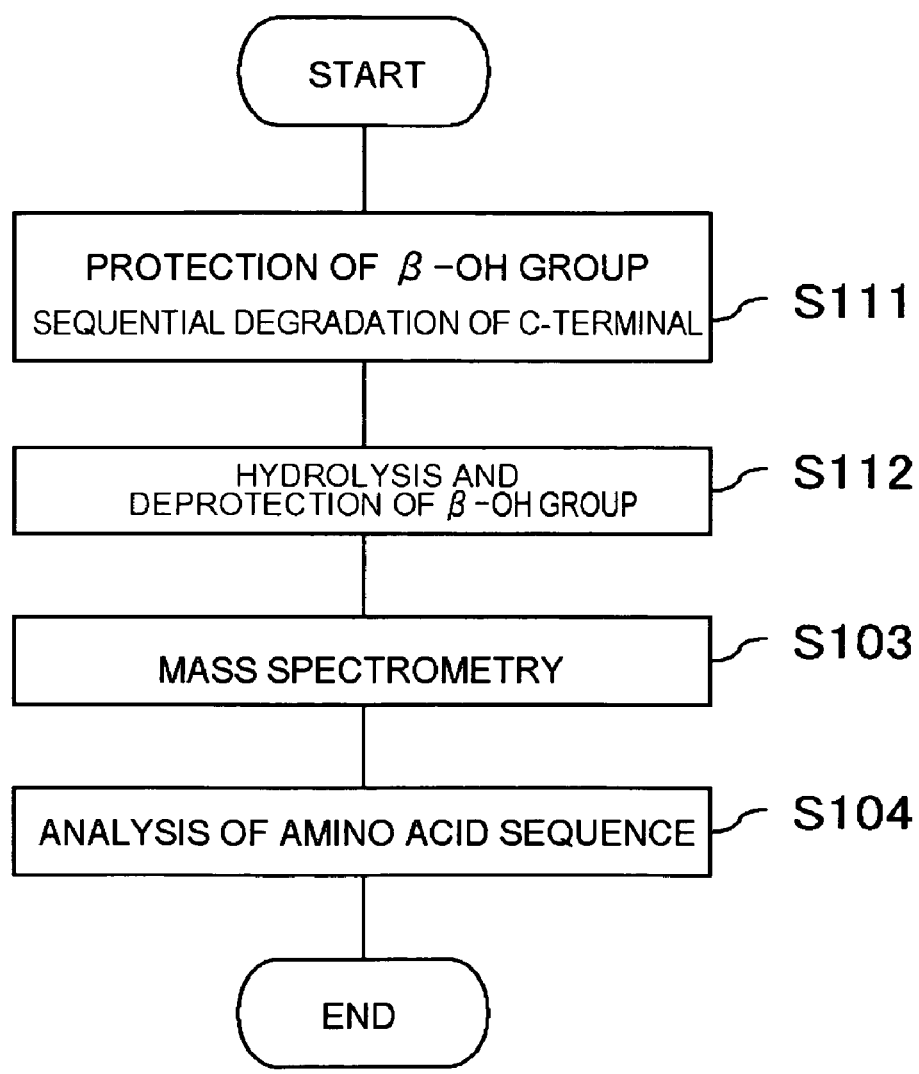
FIG. 2 is a flow chart showing the procedure of analyzing the C-terminal amino acid sequence of the peptide according to the embodiment.

FIG. 2 is a flow chart showing more specifically step 101 of sequential degradation of C-terminal and step 102 of posttreatment in the analytical procedure shown in FIG. 1. In step 101 shown in FIG. 2, the peptide is sequentially degraded while the β-OH groups of the serine and threonine residues are protected (S111). The protection of β-OH groups simultaneously with sequential degradation allows prevention of side reactions such as peptide cleavage, as will be described below. As will be described below, the amino groups at the terminal and on the side chains of peptide are also protected during protection of the β-OH groups under normal condition.

In the procedure shown in FIG. 2, the reaction products are also hydrated, and the β-OH groups are deprotected as posttreatment (S112). In this way, it is possible to form a carboxyl group reliably on the C-terminal amino acid of the peptides after one or more amino acid residues are deleted.

Figure 3:
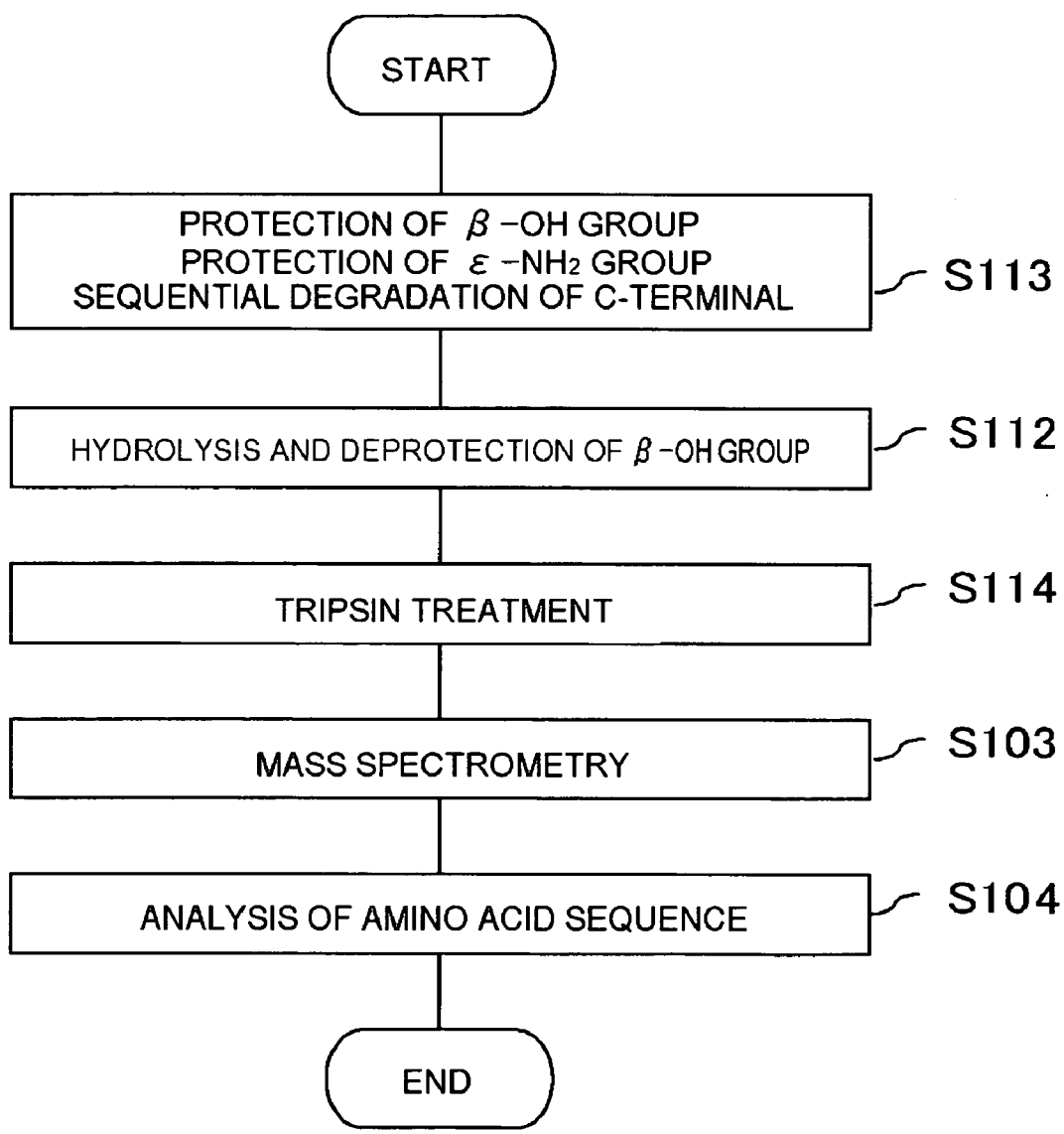
FIG. 3 is a flow chart showing the procedure of analyzing the C-terminal amino acid sequence of the peptide according to the embodiment.

FIG. 3 is a flow chart showing a procedure which is used when the analytical procedure shown in FIG. 1 is applied to a peptide having a relatively large molecular weight such as protein. Hereinafter, the method of analyzing the C-terminal amino acid sequence of the peptide according to the present embodiment will be described in detail, taking the procedure shown in FIG. 3 as an example.

The procedure shown in FIG. 3 is essentially the same as the procedure shown in FIG. 2, but differs in the following points: First, in step 113 corresponding to step 111, the β-OH and ε-$NH_2$ groups are protected, and the peptide is sequentially degraded from the C-terminal. Then in step 112 corresponding to the posttreatment in step 102, the peptides are hydrated, and the β-OH groups are deprotected. The ε-$NH_2$ groups remain protected then, and the original peptide and C-terminal-deleted peptides are fragmented at predetermined positions by using trypsin (S114). It is possible to analyze the peptides by mass spectrometry favorably by fragmentation (S103). By fragmentation using the trypsin, the peptides can be cleaved selectively at predetermined positions and fragmented. It is also possible to align the position where the original peptide and the C-terminal-deleted peptides are cleaved at the same position.

In the procedure above, it is possible to perform mass spectrometry (S103) at high accuracy and reliability, even when the molecular weight of the peptide is large. It is also possible to detect the decrease in molecular weight by sequential C-terminal degradation (S101) at high sensitivity.

As will be described below, it is possible to make the sequential degradation of C-terminal amino acids proceed selectively (S113) and prevent the side reaction of peptide bond cleavage in the peptide chain in the procedure shown in FIG. 3.

In the reaction of step 101 where the C-terminal amino acids of an analyte peptide are degraded and deleted sequentially, an alkanoic anhydride is allowed to act as an activation reagent of the C-terminal carboxyl group of the peptide chain in a moisture-free environment. The 5-oxazolone structure represented by the following Formula (III) is formed then at the C-terminal of the peptide, and the C-terminal amino acid is degraded together with cleavage of the 5-oxazolone ring. In the following Formula (III), R1 represents a side chain of the C-terminal amino acid of a peptide; and R2 represents a side chain of the amino acid residue just before the C-terminal amino acid.

[Formula 3]

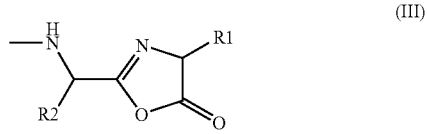

(III)

The reaction of forming the 5-oxazolone ring seems to proceed in the process represented by the following Formula (I).

[Formula 4]

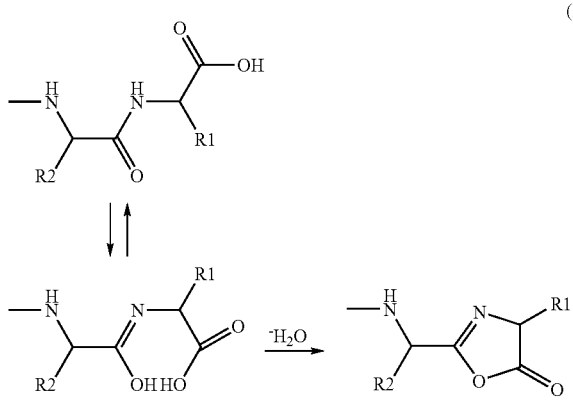

In Formula (I) above, after the keto-enol tautomerization represented by the following Formula (Ia) the hydroxyl group in the enol tautomer forms an intramolecular ester bond with the C-terminal carboxyl group, giving the 5-oxazolone ring. It is possible then to activate the C-terminal carboxyl acid group by converting it, for example, into the asymmetric acid anhydride represented by the following Formula (Ib) by using an alkanoic anhydride.

[Formula 5]

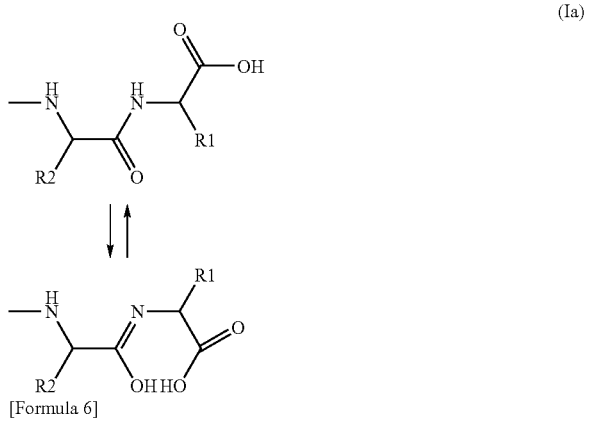

[Formula 6]

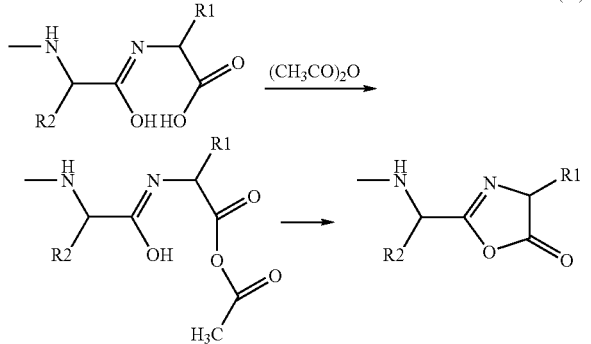

After the 5-oxazolone ring formation, it seems that the C-terminal amino acid is eliminated and a new reaction intermediate is formed, for example, through the reaction represented by the following Formula (II'), and the sequential, selective degradation of C-terminal amino acid proceeds.

[Formula 7]

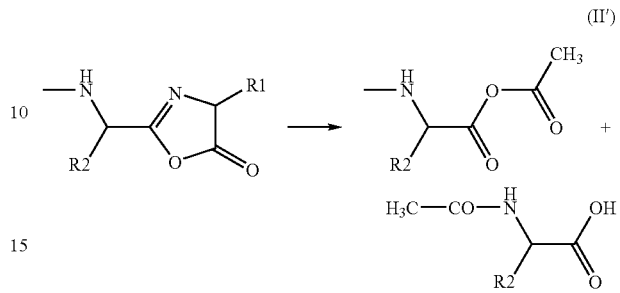

Thus in the present embodiment, it is possible to activate the C-terminal carboxyl group by using alkanoic anhydride which is a relatively mild reagent. It is thus possible to advance the sequential C-terminal degradation in a mild system containing no perfluoroalkanoic acid or perfluoroalkanoic anhydride conventionally. It is thus possible to suppress progress of side reactions such as cleavage of the peptide bonds not at the C-terminal. The sequential degradation reaction may be carried out in a moisture-free system.

Other possible side reactions in a heated environment, for example due to the side-chain hydroxyl groups (—OH) in the serine residues (—NH—CH(CH$_2$OH)—CO—) and the threonine residues (—NH—CH(CH(CH$_3$)OH)—CO—) of peptide, include the following reaction. When an N,O-acyl transfer reaction occurs between the α-amino group (—NH—) and β-hydroxyl groups of a serine residue, decomposition of the formed ester bond follows, and a side reaction of the cleavage of the peptide at the N-terminal side of the serine residue may arise. In addition, a side reaction of the cleavage of the peptide at the N-terminal side of the threonine residue may also arise on a threonine residue having a β-hydroxyl group, depending on the condition, similarly in the same reaction mechanism in N,O-acyl transfer reaction.

By the method in the present embodiment, it is possible to suppress the side reactions by performing the sequential degradation of step 113 in a dehydrated condition while using a reaction reagent substantially containing an alkanoic anhydride.

Further in step 113, β-OH and ε-NH$_2$ groups are protected, simultaneously with the sequential degradation reaction of C-terminal amino acid. The simultaneous progress of protection of β-OH and ε-NH$_2$ groups and sequential degradation of C-terminal amino acid ensures prevention of these side reactions. It also eliminates the need for a pretreatment for protection in additional to the sequential degradation and makes it possible to degrade the C-terminal amino acids stably in a simpler method.

Usually in the condition where the ε-amino group of lysine residue is protected, the N-terminal amino groups of the peptide chain is usually protected. By selecting such a condition, it is possible to prevent in advance the reaction of the C-terminal carboxyl group with the N-terminal amino groups of the adjacent peptide chain, when the C-terminal carboxy group is activated in the sequential degradation reaction of C-terminal amino acid.

It is possible in step 114 to fragment the reaction products selectively at predetermined positions by trypsin fragmentation. Thus even if the original peptide has a relatively larger molecular weight, it is possible to perform mass spectrometry (S103) after the peptide is cleaved into fragments having adequate sizes. It is thus possible to detect deletion of C-terminal amino acid residues at higher sensitivity by mass spectrometry. It is thus possible to analyze the C-terminal amino acid sequence of the peptide more reliably.

The fragmentation of peptide using the trypsin occurs selectively at the C-terminal sides of basic amino acid residues, and thus, it is possible to harmonize the cleavage positions of the original peptide and the C-terminal amino acid-deleted peptides. Thus, the C-terminal-sided fragment peptide derived from original peptide has a sequence identical with the sum of the C-terminal-sided fragment peptide derived from a C-terminal amino acid-deleted peptide and a predetermined number of amino acid residues at the C-terminal side. It is thus possible to specify the kind of the amino acid residues deleted, by comparing the molecular weights of these peptides and calculating the decrease in molecular weight by sequential degradation.

Among basic amino acid residues, a lysine residue may be already modified naturally, for example by dimethylation or acetylation. Because the modified lysine residue is resistant to trypsin digestion, the peptide fragments formed by trypsin digestion differ, depending on whether there is modification thereon. Thus in step 113 of the analytical method shown in FIG. 3, the E-amino groups of lysine residues are protected, and the protecting groups are kept undeprotected in step 112. In this way, it is possible to eliminate the trypsin sensitivity of the lysine residues in advance. It is thus possible to perform selective fragmentation at the C-terminal-sided peptide bonds of arginine residues.

It is thus possible to fragment the stepwise degradation products in which C-terminal-sided amino acids is deleted, further into peptide fragments having a molecular weight in a molecular weight range more favorable for mass spectrometry. It is thus possible to use the trypsin treatment favorably as a treatment of adjusting the molecular weight of the C-terminal-sided peptide fragments.

After the trypsin treatment in step 114, the sample is desalted for recovery of the peptide fragments, the peptide fragments are dried, and the molecular weights of the ionic species derived from the peptide fragment mixture are measured by using a mass spectrometer. The peptide fragments desalted, recovered and dried are not salts any more, but are pure partial fragments of the original peptide. It is possible to specify the amino acids deleted from the C-terminal side by comparing the molecular weight of the C-terminal-sided peptide fragments between the series of reaction products obtained by selective stepwise C-terminal cleavage and the peptide fragment obtained by trypsin digestion of the peptide before cleavage and analyzing based on the difference.

Examples of the mass spectrometers for use in mass spectrometry (S103) include ion trap mass spectrometer, quadruple mass spectrometer, magnetic-field mass spectrometer, time-of-flight (TOF) mass spectrometer, Fourier-transform mass spectrometer, and the like. Examples of the ionization methods include electrospray ionization (ESI), matrix-assisted laser desorption/ionization (MALDI), fast atom bombardment (FAB) and the like.

Among them, for example, MALDI-TOF-MS is favorably used. Use of the MALDI-TOF-MS is effective in suppressing the deletion of part of atom groups from the amino acid residues constituting the peptide fragment in the ionization process. It is also possible to measure peptide fragments having a relatively higher molecular weight favorably. In addition, even when the analyte protein is isolated from the sample by gel electrophoresis, treated in the gel as described above, and recovered before measurement, it is possible to analyze both of the corresponding anions and cations. For that reason, use of the MALDI-TOF-MS allows analysis further higher in reproducibility.

Hereinafter, the embodiment will be described, taking the case where MALDI-TOF-MS is used for mass spectrometry as an example. In the ionization process of MALDI-TOF-MS, it is possible to measure both cationic species of the peptide fragments with proton ($H^+$) added and anionic species of peptide fragments from which a proton is eliminated. In the present embodiment, the cationic and anionic species are analyzed separately by selecting the measurement mode.

In mass spectrometry (S103), which is performed after trypsin treatment (S114), there is no arginine residue in the amino acid residues constituting the C-terminal-sided peptide fragment. On the other hand, other peptide fragments obtained in trypsin treatment (S114) contain arginine residues having a guanidino group higher in proton-accepting capacity, and thus, the cationic species derived therefrom are stabilized.

Accordingly, C-terminal-sided peptide fragments and other peptide fragments show behaviors different in relative intensity, if the results when cationic species are measured and when anionic species are measured by mass spectrometry are compared. It is thus possible to identify and specify the peaks derived from a series of C-terminal-sided peptide fragments among the multiple kinds of peaks determined by the MALDI-TOF-MS device, by using the phenomenon.

Among the cationic species in the mass spectrum, the peaks derived from peptide fragments having an arginine residue at C-terminal have a relatively stronger intensity. On the other hand, C-terminal-sided peptide fragments having no arginine residue have a carboxyl group with a proton-donating capacity at the C-terminal. Thus, among the anionic species in mass spectrum as determined in a MALDI-TOF-MS device, the peaks derived from the C-terminal-sided peptide fragments have a relatively stronger intensity.

It is thus possible to differentiate the peaks derived from the peptide fragments having an arginine residue at the fragment C-terminal and the same N-terminal-sided amino acid sequence, by using the difference in relative intensity when the mass spectra of cationic and anionic species obtained by MALDI-TOF-MS are compared. In the mass spectrum of anionic species, it is also possible to specify easily the peaks derived from the C-terminal-sided peptide fragments derived from the original peptide chain and those of a series of the peaks produced in the sequential degradation reaction of C-terminal amino acid.

The length of the peptide fragment supplied to the mass spectrometric analysis in step 103 is, for example, less than 20 to 30-amino acid residues. In this way, it is possible to ionize the peptide fragments reliably during mass spectrometric analysis.

In the analysis of amino acid sequence in step 104, the kind of the amino acid causing a change in molecular weight is specified, by measuring the decrease in molecular weight associated with the sequential degradation of C-terminal amino acids, based on a series of peaks having a relatively larger intensity in the molecular weight measurement of anionic species.

C-terminal-sided peptide fragments having no arginine residue have at least an α-amino group of the N-terminal amino acid residue by trypsin digestion. These peptide fragments show corresponding peaks in the mass spectrum of cationic species. It is thus possible to verify the sequential result on the kind of amino acid, by using the molecular weight of the corresponding peak observed in the mass spectrum of cationic species.

Although the trypsin treatment is performed in step 114 of the procedure shown in FIG. 3, any method may be used in the present embodiment, if it cleaves the original peptide and the C-terminal-sided amino acid residue-deleted peptides selectively at predetermined positions. The methods other than trypsin treatment include, for example, enzyme digestion by using protease having cleavage-site specificity, such as V8 protease that cleaves the C-terminal side of glutamic acid residue specifically. Alternatively, a cleavage method of using a chemical reagent such as CNBr that specifically cleaves the C-terminal-sided amide bond of methionine residue may also be used.

Further, the method of protecting or deprotecting amino acid residue side chains may be chosen arbitrarily according to the properties of the amino acid residue at the cleavage site. The amino acid residues may be protected in a step additionally formed before step 101 in FIG. 1.

Hereinafter, the analytical method according to the present invention will be described more in detail, separately when the analyte peptide is retained in the gel, for example of electrophoresis, and when the analyte peptide is a dry sample.

First Embodiment

In the present embodiment, a procedure of treating a peptide retained in gel and analyzing the treated peptide by mass spectrometry will be described. The processing in steps 113, 112, and 114 in FIG. 3 is performed while the peptide is contained in gel.

The peptide may be previously purified by gel electrophoresis. The peptide retained in gel after electrophoresis is not isolated therefrom, and the C-terminal amino acids of the peptide are sequentially degraded while the peptide is retained in the gel.

Figure 4:
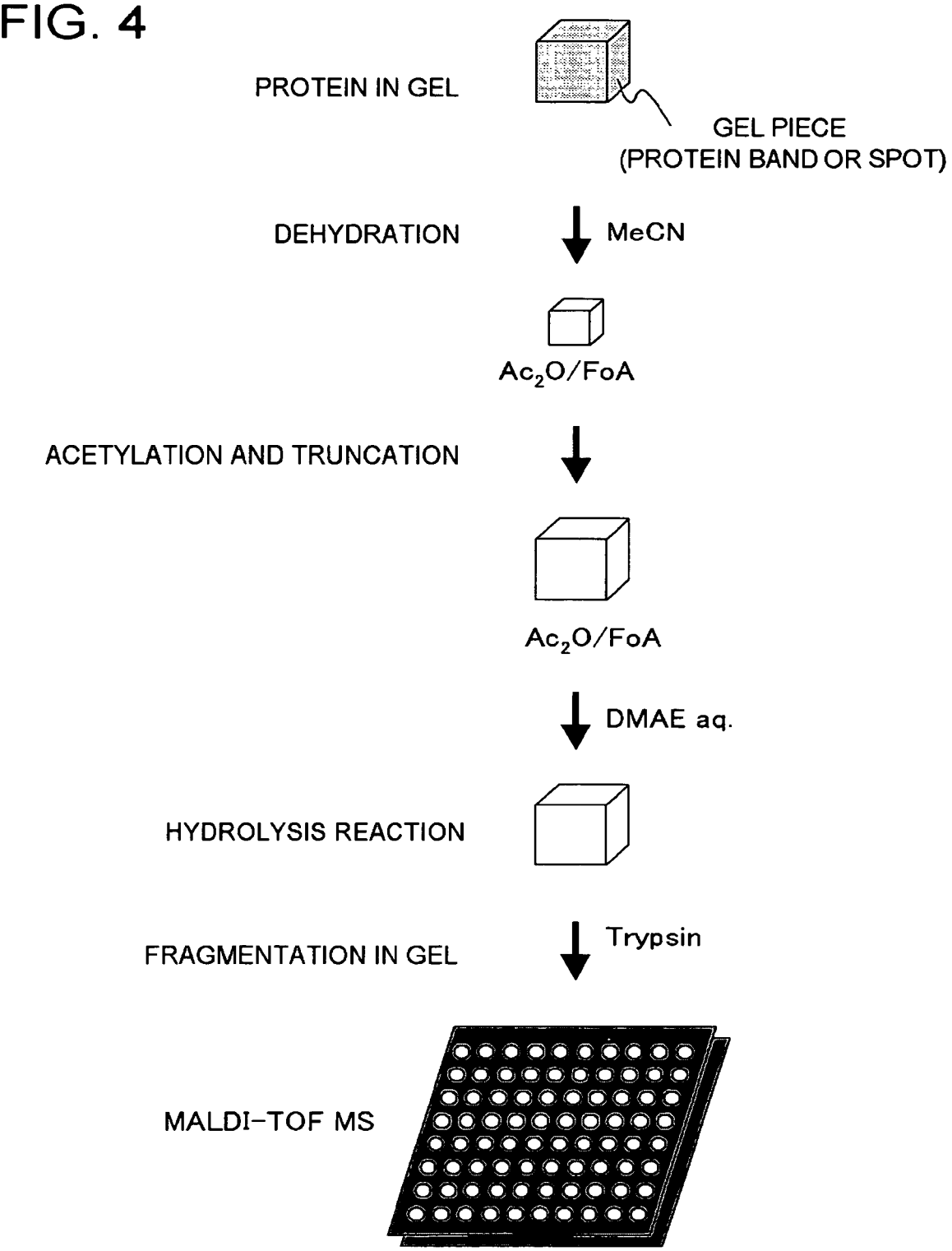
FIG. 4 is a chart showing the procedure of analyzing the C-terminal amino acid sequence of the peptide according to the embodiment.

FIG. 4 is a chart showing the procedure of the method of determining the C-terminal amino acid sequence of the peptide according to the present embodiment. The "acetylation-truncation" in FIG. 4 corresponds to step 113 shown in FIG. 3. Alternatively, the "hydration reaction" in FIG. 4 corresponds to step 112 shown in FIG. 3. The "fragmentation in gel" in FIG. 4 corresponds to step 114 shown in FIG. 3. And, the "MALDI-TOF-MS" in FIG. 4 corresponds to step 103 shown in FIG. 3. Hereinafter, each step will be described in detail with reference to FIGS. 3 and 4.

A peptide sample previously isolated by gel electrophoresis and retained in gel is first subjected to sequential C-terminal degradation associated with introduction of a protecting group (S113). The gel is previously cut into small pieces. For example, the gel is cut into cubes of 0.5 to several mm cubic.

Water in the gel is removed previously. In this way, the reaction is performed in step 113 stably. The peptide isolated by gel electrophoresis is retained in the pore formed in the gel. Thus for removal of water solvent impregnated in the gel, it is possible to use a method of allowing only water to dilute and elute into a polar aprotic solvent dissolving no gel substance that has affinity with water. It is possible to keep the analyte peptide retained as an isolated spot or band in the gel even after dehydration operation, by using the method.

In the case of a polyacrylamide gel, the affinity of the polar aprotic solvent for use in dehydration to the gel is generally lower than of the aqueous solvent to the gel. Thus, as shown in FIG. 4, addition of such a solvent leads to salvation of the gel and removal of the water solvent, which is essential for preservation of the pore size of the fine-pore gel structure, and consequently to decrease in the bulk volume of the gel.

Hereinafter, the present invention will be described, assuming that the gel material is polyacrylamide. When the material for the gel cube is polyacrylamide, the polar aprotic solvent for use in dehydration is, for example, a hydrophilic solvent, and examples thereof include nitrile of 4 or less carbon atoms such as acetonitrile ($CH_3CN$), ketones having 4 or less carbon atoms such as acetone, and the like. These polar aprotic solvents vaporize more easily than water. Vaporization of the polar aprotic solvent, that is, drying of the gel, results in decrease in bulk volume and shrinkage of the gel.

When the gel is dehydrated with acetonitrile, the gel cube is, for example, immersed in acetonitrile repeatedly several times. For example, the gel cube is immersed three times at room temperature for 20 minutes. If the gel cube is already stained with a dye such as CBB (Coomassie Brilliant Blue), the dye is removed along with substitution with the solvent, and the gel cube becomes decolorized. Thus, it is possible to recognize completion of the solvent substitution roughly by the change in color.

In step 113, protecting groups are introduced on the peptide, and the C-terminal amino acids thereof are degraded sequentially. An example of the reaction reagent for use in the simultaneous introduction of protecting groups on the peptide and sequential degradation of C-terminal amino acid is an alkanoic anhydride. Specifically, a solution containing an alkanoic anhydride in a dipolar aprotic solvent is used. It is possible to make the alkanoic anhydride act on the peptide retained in gel and cause the reaction represented by Formula (III) above at the C-terminal of the peptide, by immersing the gel cube in the solution. In the reaction, the C-terminal amino acids are degraded sequentially via a 5-oxazolone structure along with cleavage of the 5-oxazolone ring. The peptide is then activated at the C-terminal carboxyl group by the alkanoic anhydride, and forms, for example, the asymmetric acid anhydride represented by Formula (Ib) above.

By using a solution of an alkanoic anhydride in a dipolar aprotic solvent, it is possible to advance the sequential reaction under mild condition without use of a highly reactive acid such as a perfluoroalkanoic acid. The reaction gives a mixture of the original peptide and C-terminal-deleted peptides in which 1 t on C-terminal amino acids (n is a natural number) are deleted from the original peptide.

C-terminal amino acids are deleted and formation of new reaction intermediates proceeds from the 5-oxazolone ring once formed, for example, in the reaction represented by the following Formula (II'). The sequential and selective degradation of C-terminal amino acids seems to proceed continuously in this way. Accordingly, the reaction products after completion of the reaction contain intermediate products having the 5-oxazolone ring structure, other reaction intermediates having an asymmetric acid anhydride at C-terminal as impurities, in addition to the peptides formed with a carboxyl group at C-terminal.

The sequential degradation reaction of C-terminal amino acid in step 102 consists at least two-step elementary reactions of the process represented by Formula (Ib) above of forming a 5-oxazolone ring structure and the process represented by Formula (II') above of isolating a terminal amino acid by the cleavage of the 5-oxazolone ring structure. Thus, the entire reaction rate depends on the reaction rates of both these processes and also on the concentration of the alkanoic anhydride and the reaction temperature. A series of reaction products are formed in sequential reaction, and the maximum deletion length of the C-terminal amino acid sequence increases over time.

Accordingly, the processing period of the sequential degradation of C-terminal amino acid can be decided properly, mainly according to the kind and concentration of the alkanoic anhydride and the reaction temperature and also, considering the desirable amino acid length of the analyte C-terminal amino acid sequence.

The alkanoic anhydride for use in activation of the peptide C-terminal carboxyl group may be the symmetric anhydride of an alkanoic acid of approximately 2 to 6 carbon atoms. In this way, it is possible to ensure appropriate reactivity when heated to the reaction temperature. It is preferably a symmetric anhydride of alkanoic acid of approximately 2 to 4-carbon atoms. In this way, it is possible to reduce steric hindrance. Alternatively, the symmetric anhydride of a straight-chain alkanoic acid of approximately 2 to 6 carbon atoms may be used as the symmetric acid anhydride. Preferably, the symmetric anhydride of a straight-chain alkanoic acid of approximately 2 to 4 carbon atoms is used. In this way, it is possible to reduce steric hindrance. Specifically, the symmetric anhydride of a straight-chain alkanoic acid of 2 carbon atoms, that is, acetic anhydride, may be used.

The alkanoic anhydride is preferably a compound having a smaller steric hindrance in the orientation of the arrangement suitable for activation of the C-terminal carboxyl group and formation of the 5-oxazolone ring. Acetic anhydride is favorably used from the point above.

Because the alkanoic anhydride is consumed in the reaction, it is preferable to prevent decrease in its concentration, by dissolving it previously in the dipolar aprotic solvent used for swelling the gel in an amount large excess to that consumed in the reaction with peptide. For example, the sequential degradation reaction may be performed under the condition shown in FIG. 5. The concentration of the alkanoic anhydride in the reaction solution may be 1 vol % or more and 30 vol % or less, preferably 10 vol % or more and 20 vol % or less. The reaction temperature may be, for example, 50° C. or higher, preferably 60° C. or higher. In this way, it is possible to carry out the sequential degradation efficiently. The reaction temperature may be, for example, 100° C. or lower, preferably 80° C. or lower. In this way, it is possible to carry out the sequential degradation stably.

The reaction period depends on the reaction temperature and the concentration of the alkanoic anhydride contained in the dipolar aprotic solvent. A higher reaction temperature leads to increase in reaction rate and gives a series of reaction products having a desirable maximum amino acid sequence deletion in a shorter processing period. The reaction period is decided properly, also considering the period needed for swelling of the gel once contracted along with the dehydration by using a polar aprotic solvent. For example, after a polyacrylamide gel (12.5 mass %) gel is previously subjected to dehydration with acetonitrile, the period needed for re-swelling the gel is approximately three hours at 40° C. by immersing it in a dipolar aprotic solvent such as formamide as described below. Therefore, the entire reaction period may be the sum of the period for re-swelling the gel and the period needed for degrading the desirable number of amino acid residues from the C-terminal selectively.

For example, when acetic anhydride is used, the reaction period may be approximately 4 to 110 hours, as shown in FIG. 5. The reaction condition then may be, for example, at 50° C. for 110 hours, at 60° C. for 50 to 60 hours, at 80° C. for 24 hours, at 100° C. for 4 hours, or the like. A lower reaction temperature, that is, a milder condition, prevents side reactions more effectively.

On the other hand, the dipolar aprotic solvent for dissolving the alkanoic anhydride is a solvent that can penetrate into the gel and keep the gel swollen at a temperature of approximately 50 to 90° C. after gel dehydration. An organic solvent relatively smaller in molecule size and superior in affinity with the gel cube material is favorably used. It is also preferably a solvent that is dipolar enough to keep the rate of the enol tautomer high in the process of the keto-enol tautomerization in the reaction represented by Formula (I) above and is a good solvent for the solute molecule alkanoic anhydride and the reaction by-product alkanoic acid. A dipolar aprotic solvent less volatile or transpiring at the reaction temperature above is preferable.

Specifically, formamide ($HCONH_2$), for example, satisfies all the requirements above sufficiently, when polyacrylamide gel is used.

The dipolar aprotic solvent efficient in dissolving the alkanoic anhydride and the reaction by-product alkanoic acid in step 113 also dissolves water as well. The C-terminal carboxyl group activated, as it is converted into the reaction intermediate represented by Formula (Ib) above or the asymmetric acid anhydride represented by Formula (II') above, is hydrolyzed when water molecules are present in the reaction system and returns back to the original structure having a carboxyl group at the terminal. For prevention of the inactivation process, it is preferable to keep the reaction system in a moisture-free dry atmosphere during reaction in the solution of the dipolar aprotic solvent.

Among the amino acid residues in the analyte peptide, for example, methionine has a sulfur atom, which may be oxidized by the oxygen contaminated in the system, and may cause a change in molecular weight. It is possible to improve the accuracy in the molecular weight measurement by mass spectrometry (S104) by preventing the oxidation by oxygen.

For keeping the reaction system in a moisture- and oxygen-free dry atmosphere, it is possible, for example, to use a method of making the reaction system tightly sealed state, preventing penetration of moisture and oxygen from outside, and performing operations of adding and withdrawing the liquid used in the reaction under the atmosphere of dried nitrogen or an inert gas such as argon. Alternatively, a compound having a reductive sulfanyl group (—SH) such as DTT which has oxidation inhibiting effect may be added for prevention of the oxidation.

The protection of the $\beta$-OH and $\epsilon$-$NH_2$ groups performed along with the sequential degradation of C-terminal amino acid includes, for example, N-acylation and O-acylations, respectively. These acylations can be performed, for example, by stirring the gel cube in a mixture containing an alkanoic acid added in a small amount to an alkanoic anhydride. The alkanoic anhydride becomes an electrophilic acylating agent then. Alternatively, the alkanoic acid with its proton-donating capacity becomes a catalyst for acceleration of the acylation reaction. The alkanoic acid with proton-donating capacity accelerates the reaction between the alkanoic anhydride and the amino and hydroxyl groups, resulting in N-acylation and O-acylation. FIG. 4 shows an example where the acylation is acetylation.

The alkanoic anhydride becomes polarized then in the dipolar aprotic solvent, thus allowing the N-acylation and O-acylation reactions of the amino and hydroxyl groups of peptide to proceed. In addition, when an alkanoic anhydride-derived alkanoic acid is generated as a by-product along with the N-acylation and O-acylation reactions, and shown by the N-acylation and O-acylation reactions are accelerated by catalysis effect of the alkanoic acid.

Thus in the present embodiment, by using the fact that the alkanoic acid by-produced in the gel cube diffuses or dissipates not rapidly, it is possible to use the by-product alkanoic acid remaining in the gel cube as a catalyst for acceleration of the reaction. Thus, only an alkanoic anhydride may be used as the reaction reagent in the present embodiment, unlike in the third embodiment described below. In this manner, it is possible to perform the sequential C-terminal degradation reaction and the acylation simultaneously.

Protection of the side chain amino group on the lysine-residue by N-acylation is aimed at preventing cleavage of the C-terminal-sided peptide bond of the lysine residue during the trypsin digestion treatment in step 114. For that reason, an acyl group that does not cause deprotection of the N-acyl group on the lysine-residue side chain during the hydrolysis (S112) described below is preferably selected. As for O-acylation protection simultaneously performed, an acyl group that allows sufficiently deprotection in step 112 is preferably selected.

Then, the sequential degradation reaction and acetylation reactions of C-terminal amino acid are terminated, by lowering the temperature of the reaction system and diluting and removing the reaction reagent remaining in the gel, that is, alkanoic anhydride. The mixed solution used in the sequential degradation reaction of C-terminal amino acid may be used then as the polar aprotic solvent that does not dissolve the gel material and has affinity with the alkanoic anhydride and the dipolar aprotic solvent.

The dipolar aprotic solvent used in preparation of the mixed solution may be used for dilution and removal of the reaction reagent. Alternatively, a polar aprotic solvent less contributed to stabilizing the enol intermediate may be used. In this way, it is possible to terminate the process of forming the 5-oxazolone ring structure represented by reaction formula (Ib) reliably. For example, it is possible to perform the operation of dilution or removal by using a polar aprotic solvent at the final stage of the dilution or removal of the reaction reagent. Examples of the polar aprotic solvents when polyacrylamide gel is used include nitriles having 4 or less carbon atoms such as acetonitrile, ketones of 4 or less carbon atoms such as acetone, and the like.

The products of the sequential degradation reaction of C-terminal amino acids are hydrated as posttreatment in step 112. The step is also carried out, while the peptide mixture containing a series of reaction products is retained in the gel. The gel cube is immersed in an aqueous solution dissolving the basic nitrogen-containing aromatic ring compound or tertiary amine compound, while the mixture containing a series of reaction products obtained in the sequential degradation reaction of C-terminal amino acids is retained in the gel. In this way, water molecules are allowed to act on the original peptide and C-terminal-deleted peptides in the presence of the basic nitrogen-containing organic compound, causing hydrolysis of these peptides.

The basic nitrogen-containing aromatic ring compound or the tertiary amine compound catalyzes hydrolysis reaction of the 5-oxazolone ring structures represented by Formula (II') above and the reaction intermediates (acid anhydride) during the hydrolysis. It is also possible to prevent the reaction thereof with the 5-oxazolone ring structures or the reaction intermediates (acid anhydride) not to generate by-product. Accordingly, the basic nitrogen-containing aromatic ring compound or the tertiary amine compound functions as a favorable base catalyst. As shown in the following Formula (IV), a carboxyl group is formed on the peptide C-terminal by the hydrolysis reaction.

[Formula 8]

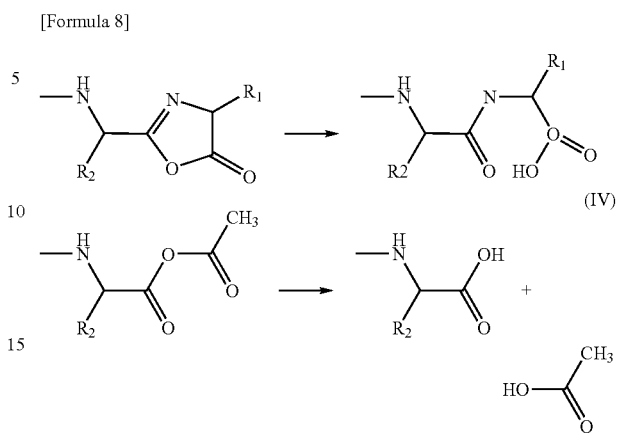

(IV)

In addition, the basic nitrogen-containing aromatic ring compound or the tertiary amine compound does not allow the reaction, for example, of a remaining C-terminal with the asymmetric acid anhydride not to form an amide bond, and also gives a homogeneous solution when added to an aqueous solution.

A monocyclic nitrogen-containing aromatic ring compound highly soluble in polar aprotic solvent may be used as the basic nitrogen-containing aromatic ring compound. Specifically, pyridine, pyridine base, or the like is used favorably. Alternatively, a compound having basicity similar to relatively low basicity of the pyridine base is used as the tertiary amine compound. Specifically, DMAE (dimethylaminoethanol: $(CH_3)_2N-CH_2CH_2OH$) and the like are used as the tertiary amine compounds.

For example, when pyridine is used, pyridine is used at a concentration of 5 vol % or more and 15 vol % or less, more specifically 10 vol % with respect to the entire volume of the aqueous solution. Alternatively when DMAE is used, DMAE is used at a concentration of 1 vol % or more and 20 vol % or less, more specifically 10 vol %, with respect to the entire volume of the aqueous solution.

The monocyclic nitrogen-containing aromatic ring compound or the tertiary amine compound is supplied to the gel holding the reaction products as an aqueous solution. In the posttreatment, the aqueous solution containing the organic base penetrates rapidly into the highly hydrophilic gel. The reaction temperature may be set to 50° C. or higher, for earlier completion of the hydrolysis reaction. When the reaction is carried out in a tightly sealed reaction container, the temperature is specifically set in the range of 100° C. or lower, considering the internal mechanical strength of the reaction container.

As shown in FIG. 5, the hydrolysis reaction may be carried out, for example, by using an aqueous DMAE solution at 10 v/v % or more and 20 v/v % or less at a temperature of 50° C. or higher and 70° C. or lower for 30 minutes or longer and 120 minutes or shorter.

The hydrolysis by using the aqueous solution containing the organic base is aimed primarily at forming a carboxyl group at the peptide chain C-terminal of reaction products, the condition in which deprotection of the protected peptide by O-acylation formed in step 113 proceeds simultaneously with formation of the carboxyl group, is selected. In the condition, N-acyl protecting groups on the amino groups at peptide N-terminal and lysine-residue side chains are not deprotected under normal reaction condition.

The gel may be re-dehydrated by diluting and removing the aqueous solution impregnated in the gel by using a hydrophilic polar aprotic solvent that does not dissolve the gel has affinity with water, and the basic nitrogen-containing aromatic ring compound or the tertiary amine compound for use in hydrolysis may be diluted and removed together with water. It is thus possible to prevent the basic nitrogen-containing aromatic ring compound or the tertiary amine compound from remaining. It is thus possible to prevent co-presence of substances formed with the addition salt of the nitrogen base with respect to the carboxyl group formed at the peptide C-terminal with the nitrogen base.

In re-dehydration, a solvent having the highest solubility in the basic nitrogen-containing aromatic ring compound or the tertiary amine compound may be used as the polar aprotic solvent. Examples of the polar aprotic solvents for re-dehydration when polyacrylamide gel is used include nitrites of 4 or less carbon atoms such as acetonitrile, ketones of 4 or less carbon atoms such as acetone, and the like.

The method of performing hydrolysis after the sequential reaction of degrading C-terminal amino acids and additionally the dilution/removal operation by using a polar aprotic solvent may be replaced with a method of performing the sequential degradation reaction of C-terminal amino acids and the hydrolysis treatment continuously.

In such a case, an aqueous solution containing the organic base is added, while the sequentual reaction of degrading C-terminal amino acids is brought to termination by lowering the reaction temperature. The alkanoic anhydride is thus inactivated and eluted form the gel. Thus, the sequential reaction of degrading C-terminal amino acids is terminated, and the reaction reagent is inactivated and eliminated. The reaction products are hydrolyzed continuously, and finally, the gel is subjected to re-dehydrated process by using a polar aprotic solvent. It is thus possible to remove the aqueous solution containing the organic base, the alkanoic acid corresponding to the alkanoic anhydride, and the dipolar aprotic solvent, and to re-dehydrate the gel. It is thus possible to perform easily a processing essentially similar to that when the washing/removal operation by using a polar aprotic solvent is provided additionally as an intermediate step.

Then in step 114, the original peptide and the C-terminal amino acid residue-deleted peptides are trypsin treated. In the step, peptide chains having a long amino acid length are fragmented selectively at predetermined positions. And in step 103, a dry mixture containing the trypsin-digested peptide fragments recovered after fragmentation is subjected to molecular weight measurement by the cationic and anionic species generated by the ionization by using the MALDI-TOF-MS method.

In step 114, the mixture containing a series of hydrolyzed reaction products is re-dehydrated and trypsin digested while it is retained in the gel. Specifically, the gel cube is immersed in a buffer solution with trypsin dissolved, and the peptide chains in the gel are subjected to trypsin enzyme-specific digestion. At that time, the amino groups at the peptide N-terminal and the amino group on the lysine-residue side chains of the peptide are protected by N-acylation. Accordingly, the peptide is selectively fragmented at the C-terminal-sided peptide bond of the arginine residues present in the peptide.

The gel used in separation of compounds different in molecular weight by gel electrophoresis such as two-dimensional electrophoresis or one-dimensional electrophoresis SDS-PAGE has a function to retain peptides having an amino acid length of equal to or more than a certain range and give each compound apparently different electrophoretic moving rate. However the gel loses its peptide-holding capacity significantly, if the peptide has an amino acid length of smaller than a threshold molecular weight.

Thus, it is possible to elute and recover a group of desirable C-terminal-sided peptide fragments easily from the gel, by preparing a series of reaction products by degrading and deleting C-terminal amino acids sequentially and then fragmenting the peptides by trypsin digestion while the peptide chains having a long amino acid length are retained.

When a peptide is cleaved selectively at the C-terminal-sided peptide bond of arginine residues, multiple peptide fragments are produced from the peptide chain having a long amino acid length. A group of desirable C-terminal-sided peptide fragments then have usually an amino acid length several times smaller than that of the original peptide chain, and are released from the gel into the trypsin solution. The trypsin solution is then desalted; the buffer solution components are removed; and the trypsin-digested peptide fragments are recovered and dried.

In the mass spectrometry in step 103, the difference between the molecular weight of a series of reaction products prepared by sequential deletion of C-terminal amino acids and the molecular weight of the original peptide is determined by using the measurement results of mass spectrometry, and the amino acid corresponding to the difference in molecular weight is specified. Accordingly, in the mixture for measurement by mass spectrometry, the fragment derived from the original peptide may usually be survived in an amount allowing specification of the molecular weights. Thus, the sequential peptide degradation in step 113 may be adjusted to a condition allowing survival of the peptide in an amount sufficient for the analysis of amino acid sequence in step 104.

Also in step 104, the C-terminal-deleted peptides and the original peptide may be fragmented together. In this way, the C-terminal-sided fragment of the original peptide and C-terminal-sided fragments of the C-terminal-deleted peptides in which a predetermined number of amino acid residues is deleted from the C-terminal can both be subjected to the mass spectrometry in step 103.

It is possible to analyze, for example, up to ten or more amino acids in the C-terminal amino acid sequence by mass spectrometry. Among the up to ten corresponding reaction products, the content ratio of the reaction product having the minimal content ratio is preferably at least not less than approximately ¹/₁₀ of that having the maximum content ratio. The content ratio of the surviving original peptide is also preferably at least not less than approximately ¹/₁₀ of that of the reaction product having the maximum content ratio. On the other hand, desirable information about C-terminal amino acid sequence usually concerns 10 amino acids. It is possible to satisfy the requirement on content ratio above, for example, by selecting such a processing period that approximately ten amino acid degrees are cleaved.

A MALDI-TOF-MS device may be used for molecular-weight measurement by mass spectrometry. Use of it allows accurate molecular-weight measurement of high-molecular weight peptide chains as well. During use of the MALDI-TOF-MS device, the maximum amino-acid length of the peptides is not larger than the range of approximately 30 to 50 amino acids. It is possible to ionize the peptide fragments reliably and perform measurement accurately in this way.

Alternatively, the molecular weight of the peptide with no C-terminal amino acid deleted may be preferably in the range not more than 4,000, preferably not more than 3,000. In this way, it is possible to differentiate the amino acid residues different only by one amino acid, for example Asn and Asp or Gln and Glu, at high precision, during specification of a corresponding amino acid based on molecular-weight difference. The amino acid length, which corresponds to the molecular weight above, is in the range not more than 40 amino acids, preferably not more than 30 amino acids.

In the present embodiment, because trypsin treatment is performed in step 114, the amino acid length of the desirable C-terminal-sided peptide fragments may be controlled in the amino acid range suitable for analysis in the MALDI-TOF-MS device above. Thus, even when a peptide having a long amino-acid length such as protein is used, it is possible to measure the difference between the molecular weight of a series of reaction products prepared by stepwise deletion of C-terminal amino acids and that of the original peptide reliably. Because the C-terminal-sided peptide bonds of arginine residues are cleaved selectively during trypsin treatment, it is also possible to avoid excessive increase in the total number of peptide fragments obtained.

In the analysis of amino acid sequence in step 104, the results obtained in step 103 by cationic-species-based MALDI-TOF-MS measurement and anionic species-based MALDI-TOF-MS measurement are used. In the cationic species-based molecular weight measurement, the peaks of the peptide fragments generated in trypsin digestion treatment and having an arginine residue at the C-terminal can be judged as peaks having an intensity relatively higher that that obtained in anionic species-based molecular weight measurement, because of the arginine residue. In addition, there is no arginine residue in the C-terminal sided peptide fragment of original peptide and in the C-terminal sided peptide fragments of a series of C-terminal-deleted peptides obtained by sequential degradation of its C-terminal amino acids. Thus, the peaks of these peptide-fragment ion species can be judged as peaks having an intensity in anionic species-based molecular weight measurement relatively higher than that in cationic species-based molecular weight measurement.

Because the anionic species corresponding to a series of C-terminal-sided peptide fragments have a relatively higher intensity in the molecular weight measurement of anionic species, it is possible to monitor the decrease in molecular weight associated with the sequential degradation of C-terminal amino acids in a simpler way, based on the molecular weights measured by anionic species-based measurement. Thus by calculating the decrease in molecular weight due to deletion of an amino acid residue for each of the C-terminal-deleted peptides shorter than the original peptide by 1, 2, t o n (n is a nature number) C-terminal residues and by comparing the decrease with the molecular weights of amino acid residues, it is possible to determine the amino acid sequence from the C-terminal.

In the present embodiment, although glutamine and lysine residues have the same formula weight, it is possible to differentiate both, because the side chain of the lysine residue is N-acylated.

Conversion of the amide bond into the enol tautomer and the subsequent formation of the 5-oxazolone ring structure are essential in the reaction deleting C-terminal amino acid, as shown in Formula (Ib) above; and thus, the degradation reaction terminates when a proline residue which is a cyclic amino acid not having a carbonyl group (C=O) and an imino group (—NH—) constituting an amide bond, becomes the C-terminal amino acid. It is thus possible to estimate that the causative amino acid residue is proline, by confirming that there is no further deletion of C-terminal amino acid even when the processing period is elongated.

Even if the hydroxyl groups present in the serine and threonine residues, the N-terminal amino group, and the ε-amino groups of lysine residues in peptide are not protected by O-acylation or N-acylation in step 113, the O- and N-acylation reactions progress concurrently during the sequential degradation reaction, because an alkanoic anhydride is allowed to react in the sequential degradation of C-terminal amino acid. It is thus possible to obtain an advantage of competitively inhibiting the side reactions such as N,O-acyl rearrangement reaction due to the hydroxyl groups present in the serine and threonine residues. It is possible to prevent shedding of peptide more reliably, by selecting a condition in which protection by O-acylation and N-acylation proceeds simultaneously with the sequential degradation reaction of C-terminal amino acids. Thus, the method in the present embodiment allows more reliable determination of the molecular weight of peptide fragments.

When there are many contaminants having an acetylated serine residue or an acetylated threonine residue in the reaction product finally obtained, because the difference in molecular weight between a polyacetylated product and a deacetylated product is a multiple of the formula weight 42, specifically 84, 126, or 168, which is similar to the formula weight 87 of serine residue (—NH—CH(CH$_2$OH)—CO—)), the formula weight 128 of glutamine residue (—NH—CH (CH$_2$CH$_2$—CONH$_2$)—CO—), the formula weight 129 of glutamic acid residue (—NH—CH(CH$_2$CH$_2$—COOH)—CO—), or the formula weight 170 of N-acetyl lysine residue (—NH—CH(CH$_2$CH$_2$CH$_2$CH$_2$NH—COCH$_3$)—CO—), there is a concern that such polyacetylated products may be regarded falsely as main peaks and the deacetylated products as amino acid-deleted products.

In the present embodiment, selected is a condition in which deprotection of the O-acylation protection on serine residue and threonine residue is sufficiently proceeded by hydrolysis in the posttreatment step. It is thus possible to identify each peak reliably. The difference in formula weight between the remaining acetyl groups and the amino acid residues having a similar formula weight is 2 to 3. In the present embodiment, in which measurement of the molecular weights of the fragments is performed at an accuracy allowing differentiation of glutamine residue and glutamic acid residues having a formula-weight difference of 1, it is possible to prevent incorrect determination of peaks by performing molecular weight measurement after peptide fragmentation.

In the method in the present embodiment, an analyte protein is isolated from a sample containing multiple kinds of proteins, for example, by gel electrophoresis such as two dimensional electrophoresis or one-dimensional electrophoresis SDS-PAGE. For that reason, it is possible to estimate the approximate molecular weight for the isolated protein. It is thus possible to obtain fragments suitable for mass spectrometry in a simple method, by performing a series of chemical processings including fragmentation such as trypsin treatment according to the estimated molecular weight.

Also in the present embodiment, the analyte peptide sample is N— and O-acylated with an alkanoic anhydride, as it is retained in gel. Liquid-phase reaction in a dipolar aprotic solvent proceeds sufficiently even without acid catalysis of the alkanoic acid having a proton-donating capacity. It is hence possible to perform analysis in a simpler manner by previously eliminating the operation of isolating and recovering an analyte protein from the isolated spot (or band). It is also possible to determine C-terminal amino acid sequence at the same accuracy, independently of the recovery rate in the isolation/recovery step.

In the present embodiment, the conventional SDS-PAGE method, which is a electrophoresis formed in one dimensional direction, as well as two-dimensional electrophoresis method may be used for gel electrophoresis. In the peptide sample isolated by two-dimensional electrophoresis, because contaminants are further prevented from entering thereto, it is possible to determine the C-terminal amino acid sequence with a smaller amount of sample by the present embodiment method.

During isolation by gel electrophoresis in advance, if the analyte peptide is a peptide forming a —S—S— bond between the cysteine residues in the molecules, the electrophoresis may be performed in a reduced state after addition of a reducing agent such as 2-sulfanylethanol (HS—$C_2H_2$—OH: 2-mercaptoethanol) or DTT (dithiothreitol: threo-1,4-disulfanyl-2,3-butanediol), to give a single spot. Alternatively, the intramolecular —S—S-bond between cysteine residues may be reduced previously and the reduced cysteine carboxymethylated, for example, with iodoacetic acid, for obtaining a single spot. It is thus possible to raise the efficiency of the trypsin digestion (S114), by converting such a peptide into a linear peptide having no intramolecular —S—S— bond between cysteine residues.

Also in the present embodiment, step 113 may be divided into two steps, a pretreatment step of introducing protective groups on the peptide and performing sequential degradation of C-terminal amino acids.

In such a case too, the alkanoic anhydride which is an electrophilic acylating agent, is used as the reagent for N-acylation and O-acylation reactions of peptide in the pretreatment step. The alkanoic anhydride is, for example, a substance reactive in N-acylating the side chain amino group on the lysine-residue at a temperature of approximately 30 to 80° C. Specifically, the alkanoic anhydride used is the symmetric anhydride derived from an alkanoic acid of approximately 2 to 6 carbon atoms. The symmetric anhydride derived from an alkanoic acid of approximately 2 to 4 carbon atoms is preferably used, for reduction of steric hindrance.

Alternatively, the symmetric anhydride of a straight-chain alkanoic acid of approximately 2 to 6 carbon atoms may be used. For reduction of steric hindrance, the symmetric anhydride of a straight-chain alkanoic acid of approximately 2 to 4 carbon atoms is used preferably. If a symmetrical alkanoic anhydride is used, by-product alkanoic acid can be made identical species. By using the identical species of alkanoic anhydride and alkanoic acid, it is possible to prevent the different acyl group from mixing in finally obtained N-acylation and O-acylation protecting groups, even if an acyl group-exchange reaction occurs during progress of the N-acylation and O-acylation reactions. Accordingly, if some of the O-acylation protecting groups which are not deprotected remain in the hydrolysis in step 112, the difference in molecular weight thereof with the deprotected product is already known, and thus, it is possible to identify the peaks due to contaminants easily. For example, acetic anhydride may be used as the alkanoic anhydride.

The dipolar aprotic solvent may be a solvent causing re-swelling of the gel. Thus, an organic solvent relatively lower in molecule size and superior in affinity with the gel material may be used. Alternatively, a highly dipolar solvent that induces intramolecular polarization of the alkanoic anhydride during the N-acylation and O-acylation reaction may be used. The solvent may be a dipolar aprotic solvent less volatile or transpiring at the temperature of the pretreatment reaction. For example, formamide ($HCONH_2$) satisfies all requirements above sufficiently, when used with polyacrylamide gel.

The alkanoic anhydride polarizes intramolecularly in the dipolar aprotic solvent and reacts with the amino groups in peptide as an electrophilic reagent. Thus, the N-acylation reaction progresses sufficiently even at a relatively low temperature of approximately 30° C. degree or higher. The reaction temperature is usually set, for example, to 50° C. or higher for acceleration of the reaction. When the acylation reaction is carried out in a tightly sealed reaction container, the temperature is preferably adjusted, for example, to 100° C. or lower, considering the internal mechanical strength of the reaction container.

Thus, the acylation may be performed, for example, by using a formamide solution containing 20 v/v % acetic anhydride at a temperature of approximately 50 to 60° C. for 2 to 4 hours. The sequential degradation of C-terminal amino acid described above in step 113 is performed after the pretreatment.

Second Embodiment

In the analytical method described in the first embodiment, the sequential C-terminal degradation (S113) is performed under mild condition by using an alkanoic anhydride. Thus, if the sequential degradation reaction is performed especially at low temperature, the reaction period becomes elongated. In the present embodiment, a method of shortening the period of the sequential degradation reaction described in the first embodiment by adding a reaction accelerator to the system will be described.

The reaction accelerator for use is a basic nitrogen-containing aromatic ring compound. The basic nitrogen-containing aromatic ring compound is, for example, a pyridine base or the derivative thereof. The pyridine base, which functions as a proton acceptor, for example, accelerates removal of the protons released by acylation of amino groups. Concrete examples of the pyridine bases include pyridine, picoline (methylpyridine), lutidine (dimethylpyridine), collidine (trimethylpyridine), ethylmethylpyridine, parvoline (tetramethylpyridine), and the like. Other basic nitrogen-containing aromatic ring compounds include azaarenes in fused ring system. Concrete examples thereof include bicyclic basic nitrogen-containing aromatic ring compounds such as quinoline, isoquinoline, and indole, and the derivatives thereof. Other examples include azaanthracenes such as benzoquinoline, benzoisoquinoline, and acridine, and tricyclic basic nitrogen-containing aromatic ring compounds such as phenanthridine; and the derivatives thereof.

Figure 6:
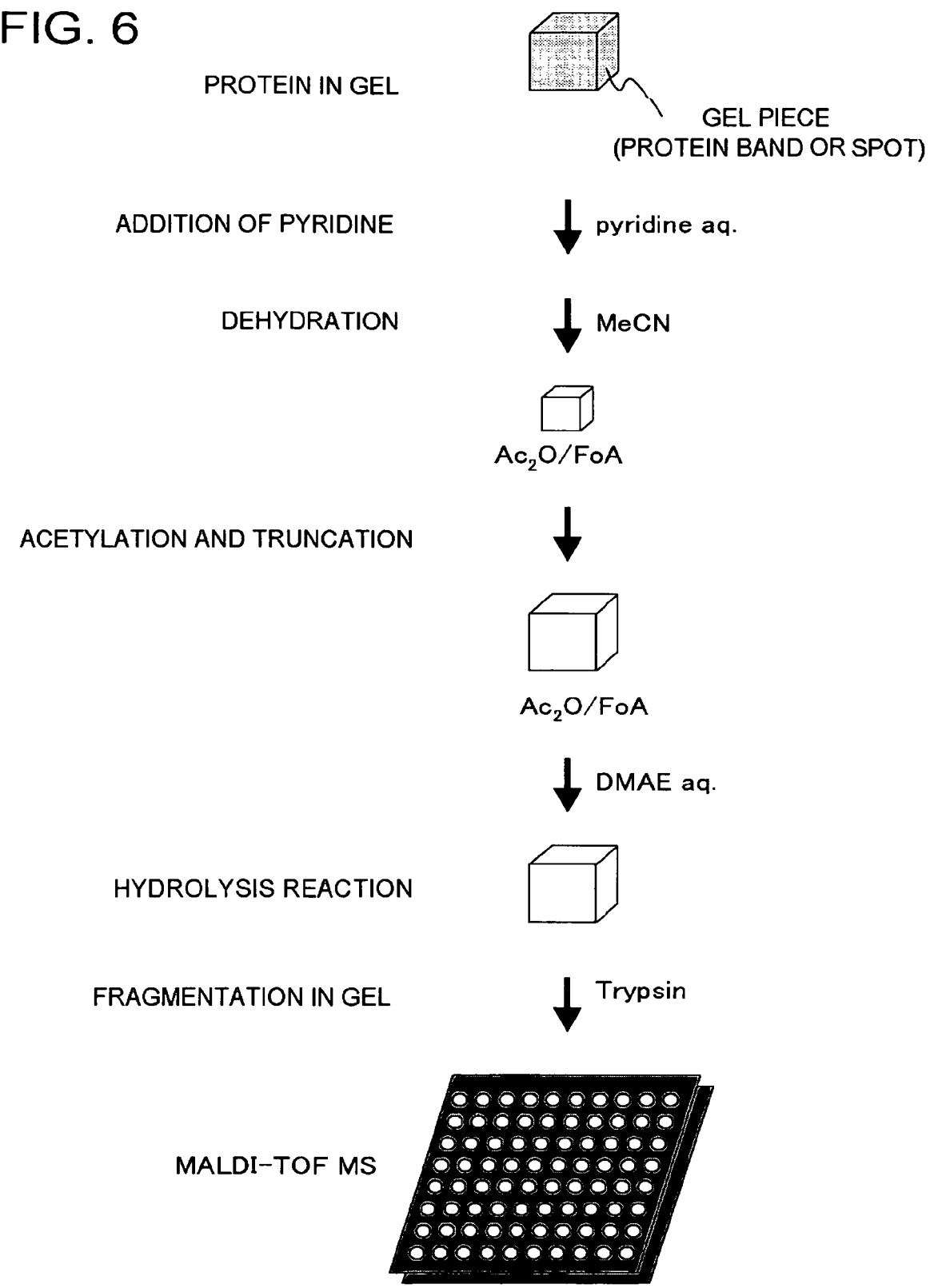
FIG. 6 is a chart showing the procedure of analyzing the C-terminal amino acid sequence of the peptide according to the embodiment.

FIG. 6 is a chart showing the procedure of analyzing C-terminal amino acid sequence in the present embodiment. The basic configuration of the procedure shown in FIG. 6 is the same as that in FIG. 4, but differs in that the gel is immersed in a pyridine solution before it is dehydrated. The dehydration of the gel after immersion in an aqueous pyridine solution accelerates truncation (step 113 in FIG. 3). It is presumably because a trace amount of pyridine is retained in the gel even after solvent substitution.

The pyridine concentration in the aqueous pyridine solution into which the gel is immersed may be, for example, 1 v/v % or more and 40 v/v % or less, and preferably 10 v/v % or more and 30 v/v % or less. In this way, it is possible to accelerate the sequential C-terminal degradation reliably. The gel may be immersed three times consecutively at room temperature for 20 minutes. If the gel is stained then, for example, with CBB, it is possible to visually monitor the degree of solvent substitution by observing the progress of decoloration. For example, the solvent substitution may be terminated when the gel is almost decolorized.

For example, when the gel is immersed in 1 v/v % pyridine solution previously, it is possible to shorten the reaction in step 113 to 10 to 20 hours at 50 to 80° C. Alternatively, for example, when the gel is immersed in 20 v/v % pyridine solution previously, it is possible to shorten the reaction in step 113 to approximately 5 minutes to 4 hours at 50 to 80° C., more specifically to approximately 10 minutes to 1 hour at 60° C. By immersing the gel in a solution containing a basic nitrogen-containing aromatic ring compound, it is possible to shorten the period of step 113 markedly, compared to the condition without use of pyridine shown in FIG. 5.

A method of carrying out the reaction under a pressurized condition may be employed instead of the method of adding a reaction accelerator, as a method of accelerating the sequential reaction in step 102. It is then possible to accelerate the degradation reaction, by placing the gel previously immersed in a reaction solution in a pressurized chamber and applying a pressure, for example, of approximately 300 to 800 MPa, more specifically approximately 600 MPa.

Third Embodiment

In the embodiments above, the proteins in the gel may be crosslinked with a crosslinking agent to form a network structure before sequential degradation. In this manner, it is possible to prevent elution of the proteins from the gel. It is thus possible to prevent elution of the sample from gel during the C-terminal sequential degradation reaction in the gel. Accordingly, it is possible to raise the intensity of the peptide-derived signals in the mass spectrometry above in step 103 described above in FIGS. 1 to 3 and the reliability and accuracy of the analysis of amino acid sequence in step 104 in FIGS. 1 to 3.

The crosslinking agent for use is, for example, a compound having binding groups at the both terminals. For examples, aldehyde group-containing compounds such as formaldehyde and glutaraldehyde are used efficiently. These aldehyde group-containing compounds form chains in various lengths by polymerization. The aldehyde groups present in or at the terminals of the polymerized aldehyde chain bind to the lysine residue in protein, forming a network structure. Thus, proteins are crosslinked to form a network structure in network-structured gel, and entanglement of the gel and the protein results in prevention of elution of the protein.

In the crosslinking reaction, it is preferable to select, considering the reactivity of the crosslinking agent, such a condition that crosslinking reaction of the lysine residues present close to the peptide C-terminal are prevented. In this manner, it is possible to assure high intensity of the signals derived form the analyte peptide more sufficiently in the mass spectrometric analysis in step 103.

When glutaraldehyde is used as the crosslinking agent, it is possible to perform immobilization with glutaraldehyde for example, by immersing the gel in an aqueous solution containing glutaraldehyde at a concentration of 1 pmol/μL or more and 1,000 nmol/μL or less for 30 minutes or more and 2 hours or less, before the sequential C-terminal degradation in step 101 of FIG. 1. The reaction condition when glutaraldehyde is used as the crosslinking agent will be described in more detail in Examples described below.

Fourth Embodiment

In the present embodiment, the analytical procedure when the analyte peptide is a dry sample will be described. The peptide is, for example, a dry sample of a protein previously isolated are generated. In the present embodiment, a method of supplying a dry vapor is used, replacing the method used in the first embodiment of performing a liquid phase reaction by allowing a reaction reagent to penetrate into the gel.

Also in the present embodiment, the protection of β-OH and ε-$NH_2$ groups in step 113 (FIG. 3) is performed, for example, respectively by O-acylation and N-acylation. Also in the present embodiment, N-acylation and O-acylation and sequential degradation of C-terminal amino acid are preformed in two stages in step 113. Thus, the N-acylation and O-acylation is equivalent to pretreatment before the sequential degradation of C-terminal amino acid.

The N-acylation and O-acylation may be specifically, for example, acetylation also in the present embodiment. The acylation reaction is performed, for example, by allowing a vapor of an alkanoic anhydride and an alkanoic acid supplied from a mixture of the alkanoic anhydride and a small amount of the alkanoic acid to react with a dry sample of an analyte peptide under a dry atmosphere at a temperature of about 10 to 60° C. In this way, it is possible to perform protection by N-acylation without side reaction of the peptide such as cleavage.

The side-chain hydroxyl groups of the serine and threonine residues present in the peptide are also protected by O-acylation. In addition, the side-chain phenolic hydroxyl groups of the tyrosine residues present in the peptide are also partially O-acylated, although its reactivity is different. It is thus possible to protect the side-chain amino groups of lysine residue and the side-chain hydroxyl groups of serine and threonine residues into the state unreactive in side reactions.

The vapor of alkanoic anhydride and alkanoic acid is supplied, for example, by a method of vaporizing a mixture of an alkanoic anhydride and a small amount of an alkanoic acid in an air-tight reaction container while heating the entire reaction container to a temperature of approximately 10° C. to 60° C. and keeping the heat.

The alkanoic acid and alkanoic anhydride are preferably those giving a desirable partial pressure at a temperature of approximately 10° C. to 60° C. Concrete examples of the alkanoic anhydride for use include those described in the first embodiment.

The symmetrical alkanoic anhydride is more preferably the symmetric anhydride of the alkanoic acid added in a small amount. In this way, it is possible to make the alkanoic anhydride and the alkanoic acid identical species. Specifically, for example, the combination of acetic anhydride and acetic acid may be used.

The alkanoic anhydride may be the same as the alkanoic anhydride used in the sequential degradation derived from C-terminal amino acid performed after pretreatment in step 113. It is thus possible to keep the vapor pressure favorable during a series of reactions.

The ratio of the alkanoic acid added in the mixture in which an small amount of an alkanoic acid is added to an alkanoic anhydride may be preferably in the range of 2 to 10 vol % with respect to the total volume of the alkanoic anhydride and alkanoic acid. Specifically, for example, the addition ratio of the alkanoic acid added may be 5 vol %.

The reaction temperature of pretreatment is, for example, 10° C. or higher and 60° C. or lower as described above. The reaction temperature may be selected around room temperature or in a range slightly higher than room temperature. The temperature may be, for example, 15° C. or higher and 50° C. or lower.

The rate of acylation reaction depends on the partial pressure (gas phase concentration) of the alkanoic anhydride and alkanoic acid used and also on the reaction temperature. Thus, the pretreatment reaction period may be selected properly, mainly according to the reaction temperature. For example, when the reaction temperature is selected to be 50° C., the reaction period may be 1 hour or shorter, for example, 30 minutes. Pyridine may be added in a catalytic amount, for example 0.1 vol % or more and 1.0 vol % or less with respect the total amount of the alkanoic anhydride and alkanoic acid, for the purpose of accelerating the acylation reaction with the alkanoic anhydride and alkanoic acid. Addition of a pyridine base, which functions as a proton acceptor, accelerates removal of the protons released along with acylation of amino groups further.

When the analyte peptide forms an oxidized —S—S— bond, for example, between cysteines in adjacent peptides or when it contains cysteines forming a —S—S— bond in the same molecule, the analyte peptide may be converted into a peptide containing reduced cysteines by processing it by a common reduction method to eliminate crosslinking. Alternatively if reduced cysteines are present in the peptide, the side-chain sulfanyl groups (—SH) may be previously protected by carboxymethylation or pyridylethylation.

For example, when the analyte peptide is present in a secondary or tertiary structure as it is protein, the peptide may be unfolded previously. By destructing the high-order structure of peptide in advance, it is possible to proceed N-acylation of the side-chain amino groups of lysine residues present in the peptide reliably, in the condition of protecting the N-terminal amino group by N-acylation. The analyte peptide may be converted into a peptide containing reduced cysteines by processing it in a common reduction method to eliminate crosslinking, when the protein possibly contains cysteines forming a —S—S— bond in the molecule. For reduced cysteines present in the peptide, the side-chain sulfanyl groups (—SH) may be previously protected by carboxymethylation or pyridylethylation.

The pretreatment may be performed by a reaction procedure of placing a mixed liquid of an alkanoic anhydride and a small amount of an alkanoic acid in an air-tight reaction container, evacuating and sealing the reaction container after the vapor pressure is reduced by cooling the liquid mixture once, heating the mixed liquid to a reaction temperature, and thus, vaporizing the alkanoic anhydride in the container. It is possible to prevent penetration of water into the reaction container more reliably by using the procedure.

Vacuum evacuation may be performed not to make oxygen remain in the reaction system. It is thus possible to prevent the change in formula weight by oxidation of the sulfur present in the methionine residues with oxygen, even when the analyte peptide contains methionine residues. Thus, it is possible to obtain high accuracy in molecular weight measurement.

A small amount of pyridine vapor may be co-present during the pretreatment. In this way, it is possible to form a weak addition salt with respect to the peptide C-terminal carboxyl group with the pyridine base and to make the peptide C-terminal carboxyl group protected from the C-terminal carboxyl group-activating reaction represented by reaction formula (Ia) above and the side reactions derived therefrom. A weakly basic nitrogen-containing heteroaromatic ring compound that is easily distillable under reduced pressure such as pyridine base may be used for protection by addition salt. The addition salt-based protection is easily deprotected by removing the pyridine base under reduced pressure in a dry-up operation additionally placed before completion of the pretreatment step. The addition salt-based protection also has a function to protect the carboxyl groups of amino acid side chains and thus to prevent the unneeded side reactions derived from the carboxyl group of amino acid side chains at the same time.

The reaction reagent remaining in the reaction container is removed after pretreatment reaction, and the sequential degradation reaction of C-terminal amino acids is initiated.

In the reaction, a vapor-phase alkanoic anhydride is allowed to react with the dry sample of the peptide protected by N-acylation under a dry atmosphere, for example, at a temperature in the range of 50° C. or higher and 100° C. or lower for a period, for example, of 4 hours or longer and 110 hours or shorter. The degradation reaction of the C-terminal amino acid occurs via the 5-oxazolone structure represented by Formula (III) above, along with cleavage of the 5-oxazolone ring.

Any one of various kinds of alkanoic anhydrides may be used, if it gives an appropriate vapor pressure when heated to the reaction temperature. The reaction temperature above is preferably selected, so that a sufficient vapor pressure is provided. For example, the symmetric anhydride of an alkanoic acid of 2 to 6 carbon atoms, preferably of 2 to 4 carbon atoms, may be used. Examples of the symmetric acid anhydrides for use include symmetric anhydrides of a straight-chain alkanoic acid of 2 to 6 carbon atoms, preferably of 2 to 4 carbon atoms. Specifically, it may be the symmetric anhydride of a straight-chain alkanoic acid of 2 carbon atoms, that is, acetic anhydride. Because the alkanoic anhydride is used for activation of the C-terminal carboxyl group, an alkanoic anhydride having a smaller steric hindrance is preferable, and acetic anhydride is favorably used from that point too.

N-acylation of the peptide N-terminal amino group with the alkanoic anhydride occurs in this step and N-acylation protection is made in the system, similarly to the first embodiment also in the present embodiment, but it is preferable to perform pretreatment by the method above.

Because the alkanoic anhydride is consumed in the reaction, the reaction may be performed by keeping the vapor pressure of the alkanoic anhydride supplied in the vapor state in a predetermined range. For that purpose, employed is a method of placing the reaction system in an air-tight state and thus, stabilizing the vapor pressure of the alkanoic anhydride present in the system. Specifically, employed is, for example, a method of placing an alkanoic anhydride in an air-tight reaction container, evacuating and sealing the reaction container after the vapor pressure is reduced by cooling the reaction container, heating the mixed liquid to a reaction temperature, and thus, vaporizing the alkanoic anhydride in the container. In this way, it is possible to prevent penetration of water into the reaction container.

In addition, the reaction is carried out in dry atmosphere, for prevention of addition of water to the 5-oxazolone ring used in the degradation reaction to back into the original state by the moisture penetrated from outside the system. From the viewpoint above, generally, the reaction may be carried out in a tightly sealed reaction container.

Also in the step, it is possible to prevent oxidation of the sulfur in the methionine residues of peptide by removing oxygen in the reaction system and by vacuum evacuation. It is thus possible to obtain high accuracy in molecular weight measurement.

The sequential and selective degradation of C-terminal amino acids seems to proceed from the 5-oxazolone ring once formed, by delimination of the C-terminal amino acid and formation of the reaction intermediate in reactions, for example, including the reaction represented by Formula (II') above. Accordingly, the reaction product obtained in the degradation reaction contains, in addition to the peptides having a carboxyl group at C-terminal formed, intermediate products having the 5-oxazolone ring and other reaction intermediates having an asymmetric acid anhydride at C-terminal as impurities.

The reaction in the sequential and selective degradation of C-terminal amino acids at least includes two elementary processes, a process of forming the 5-oxazolone ring structure represented by reaction formula (Ib) and a process of cleavage of the 5-oxazolone ring structure, that is, terminal amino acid, represented by reaction formula (II'). Accordingly, the entire reaction rate depends on the reaction rates of these elementary processes, but mainly on the partial vapor pressure (gas phase concentration) of the alkanoic anhydride used and the reaction temperature.

A series of reaction products are formed in the sequential reaction, and the maximum deletion length of the C-terminal amino acid sequence which is deleted from the original peptide increases when the processing period is elongated.

Accordingly, the period of the sequential degradation reaction of C-terminal amino acid may be selected properly, mainly according to the partial vapor pressure (gas-phase concentration) of the alkanoic anhydride used and the reaction temperature, and also, considering the desirable amino acid length of the C-terminal amino acid fragments to be analyzed.

A higher reaction temperature leads to increase in reaction rate, and a series of reaction products having the desirable maximum amino acid deletion length can be prepared in a shorter processing period. For example, the reaction period may be shortened, for example, to 110 hours at 50° C., 50 to 60 hours at 60° C., 24 hours at 80° C., 4 hours at 100° C. A lower reaction temperature, that is to say, under a mild condition, is preferable, because it is possible to suppress side reactions more.

Then in step 112, hydrolysis is performed as a posttreatment step. The alkanoic anhydride remaining in the mixture of a series of C-terminal-deleted peptides and the original peptide is first removed in the dry state. A carboxyl group is formed on the C-terminal amino acid of the peptide residues, by supplying a vapor-phase basic nitrogen-containing aromatic ring compound or tertiary amine compound and water molecules.

Then, deprotection of the side-chain hydroxyl groups of the threonine residues and serine residues and the side-chain phenolic hydroxyl groups of the tyrosine residues present in peptide chain also proceeds. On the other hand, the N-acylation protecting groups on the side-chain amino groups of lysine residues and the amino group at the peptide chain N-terminal is not deprotected, that is, remain protected.

An aqueous solution of a basic nitrogen-containing aromatic ring compound or a tertiary amine compound may be used during hydrolysis. The monocyclic nitrogen-containing aromatic ring compound or the tertiary amine compound is allowed to act on the dry mixture sample as vapor phase, together with water molecules. The posttreatment is also preferably carried out in a tightly sealed reaction container. It is possible to prevent reaction of the remaining C-terminal with the asymmetric acid anhydride not to form an amide bond, by using the basic nitrogen-containing aromatic ring compound or the tertiary amine compound in vapor phase. It is also possible to obtain a uniform solution easily when the compound is dissolved in an aqueous solution.

The basic nitrogen-containing aromatic ring compound for use is, for example, a monocyclic nitrogen-containing aromatic ring compound giving a sufficient vapor pressure. Specifically, for example, pyridine can be used. Alternatively, the tertiary amine compound for use is a compound having a relatively weak basicity similar to that of pyridine base. Specifically, it is, for example, DMAE.

For example, pyridine may be added at approximately 5 to 15 vol %, more specifically 10 vol %, with respect to the total volume of the aqueous solution. Alternatively, DMAE may be added at approximately 1 to 20 vol %, more specifically approximately 10 vol %, with respect to the total volume of the aqueous solution.

Because water molecules are used in posttreatment, it is necessary to keep the vapor pressure at a certain level or more. For that reason, the reaction system may be heated to a temperature, for example, of 60° C. or higher. The temperature may be, for example, 100° C. or lower, considering the internal mechanical strength of the reaction container. The temperature may be, for example, 100° C. or slightly lower, for earlier completion of hydrolysis.

After hydrolysis, the reaction product is re-dried for removing the basic nitrogen-containing organic compound and water molecules and for drying the reaction product.

The processings in steps 112 and 113 above may be performed in the same reactor continuously. The dry-up operation may be performed after each step, for prevention of the reagent used in the step remaining in the peptide sample. The dry-up operation may be performed by vaporization under reduced pressure. The C-terminal amino acids cleaved in step 113 may also be removed then at the same time.

Then in step 114, the original peptide and the C-terminal amino acid residue-deleted peptides are trypsin treated. In the step, the peptide chains having a long amino acid length are fragmented selectively at predetermined positions. The trypsin digestion treatment may be performed by allowing trypsin to digest the peptides in a buffer solution. Also in the present embodiment, N-acylation-protected C-terminal-sided peptide bonds of lysine residues are not cleaved because the N-acylation protecting groups on the side-chain amino groups of lysine residue are hold, and the C-terminal-sided peptide bonds of arginine residues are selectively cleaved. After trypsin digestion, the reaction product is desalted, the buffer solution components are removed, and the trypsin-digested peptide fragments are recovered and dried.

The following steps, that is to say, steps 103 and 104 of performing molecular weight measurement of the dry mixture containing the recovered trypsin-digested peptide fragments by the MALDI-TOF-MS method and analysis of C-terminal amino acid sequence based on the measurement results, are the same as those in the first embodiment.

By the method of analyzing the C-terminal amino acid sequence of the peptide in the present embodiment, it is possible to degrade C-terminal amino acids selectively under mild condition, because the reaction reagent used substantially contains an alkanoic anhydride. Because the reactivity of the acid anhydride is low, it is possible to degrade and remove the C-terminal amino acids of the peptide sequentially, while avoiding unneeded side reactions such as fission of amide bonds at positions other than the peptide C-terminal. The degradation of the C-terminal amino acid sequence then seems to be accompanied with formation of the 5-oxazolone structure and cleavage of the 5-oxazolone ring.

The N-terminal amino group and the side-chain amino groups of the lysine residues in an analyte peptide are protected by N-acylation protection, and the hydroxyl groups present in the serine residues ($-NH-CH(CH_2OH)-CO-$) and the threonine residues ($-NH-CH(CH(CH_3)OH)-CO-$) therein are also protected by O-acylation. Thus, the analyte peptide is subjected to sequential C-terminal degradation while protected by N-acylation and O-acylation, which allows prevention of side reactions more reliably.

Thus by the method in the present embodiment, it is possible to prevent cleavage of amide bonds inside peptide, and the contamination of reaction product by the peptide fragments due to the cleavage of the amide bonds above and the reaction products derived from the peptide fragments. Thus, even when the peptide is provided as a dry sample, it is possible to perform sequential analysis of C-terminal amino acids reliably under mild condition.

In the present embodiment, it is possible to use a reactor capable of storing liquid reagents for use in the reaction and supplying each of the liquid reagents in certain amounts to a peptide sample retained in a sample container and equipped with a mechanism of holding the liquid reagents so that the reagents do not become direct contact with each other. It may be a reactor that can be evacuated to vacuum the internal of the reactor for removal of the reagents remaining after completion of reaction and tightly sealed during reaction. A material unreactive with the reagent when the vapor of the reagent is formed in the reaction container is preferably used for the reaction container wall. For example, glass is preferably used for such a reaction container. Alternatively, Teflon (Registered Trademark), for example, is used preferably as the material, for example, for stopcocks used in air-tight operation.

The sequential C-terminal degradation reaction may be accelerated by applying the method in the second embodiment to the method in the present embodiment.

The present invention has been described hitherto with reference to embodiments. These embodiments are only examples of the present invention, and it should be understood for those skilled in the art that various modifications of the present invention are possible and these modifications are also included in the scope of the present invention.

For example, the following embodiments are also included in the scope of the present invention.

(1) A method of analyzing the C-terminal amino acid sequence of an analyte peptide, including:

preparing a mixture containing a series of reaction products obtained by sequential degradation of its C-terminal amino acids from the analyte peptide by chemical means;

analyzing the difference in molecular weight between the series of reaction products and the peptide by mass spectrometry and determining the decrease in molecular weight associated with the sequential degradation of C-terminal amino acids; and specifying the series of amino acids sequential degradation, based on the decrease in molecular weight of the series of reaction products and obtaining information on the C-terminal amino acid sequence by arranging them in order from the C-terminal, wherein the degrading the C-terminal amino acids sequentially at least includes:

protecting the peptide N-terminal amino group and the side-chain amino groups of the lysine residues possibly contained in the peptide by N-acylation by acyl group derived from an alkanoic anhydride, by allowing an alkanoic anhydride and an alkanoic acid in vapor phase supplied from a mixture of the alkanoic anhydride and a small amount of the alkanoic acid to act on a dry sample of the analyte peptide under dry atmosphere at a temperature selected in the range of 10° C. to 60° C.; and additionally, degrading C-terminal amino acid at the C-terminal of the peptide, via the 5-oxazolone structure represented by General Formula (III) above, along with cleavage of the 5-oxazolone ring, by allowing a vapor-phase alkanoic anhydride to act on a dry sample of the analyte peptide protected by N-acylation protection under dry atmosphere at a temperature selected in the range of 50° C. or higher and 100° C. or lower; and a hydrolytic process of post-processing the mixture containing the series of reaction products obtained in the degrading C-terminal amino acid sequentially for removing the remaining alkanoic anhydride in dry state, hydrolyzing the reaction product peptide by allowing the water molecule to react with the reaction product peptide in the presence of a basic nitrogen-containing organic compound, while supplying a vapor-phase basic nitrogen-containing aromatic ring compound or a tertiary amine compound and water molecule by using an aqueous solution dissolving the basic nitrogen-containing aromatic ring compounds or the tertiary amine compounds, and after the hydrolytic process, removing the basic nitrogen-containing organic compound and water molecules remaining in the mixture containing the series of reaction products and re-drying the reaction product peptide, and the measuring the decrease in molecular weight associated with the sequential degradation of C-terminal amino acids includes: fragmenting the peptide having the N-terminal amino group of the peptide chain and the side-chain amino groups of lysine residues possibly contained in the peptide chain, by the selective degradation of the C-terminal-sided peptide bonds of arginine residues present in the peptide chain due to specific digestion of the peptide chain protected by N-acylation by trypsin enzyme, while allowing trypsin to digest the mixture containing a series of reaction products re-dried and hydrolyzed in a buffer solution;

recovering and drying the trypsin-digested peptide fragments after desalination and removal of the buffer solution component; and then, performing molecular weight measurement based on the cationic and molecular weight measurement based on anionic species generated by ionization on a dry mixture containing the recovered trypsin-digested peptide fragments by using a MALDI-TOF-MS method; and, among the corresponding ionic species observed both in the cationic species-based molecular weight measurement and anionic species-based molecular weight measurement, assuming that the peaks of the peptide fragments having an arginine residue at the C-terminal produced by the trypsin digestion are the peaks that give an intensity in the cationic species-based molecular weight measurement relatively larger than that in anionic species-based molecular weight measurement and that the peaks of the C terminal peptide fragments derived from original peptide and peaks of the C terminal peptide fragments derived from the series of reaction products obtained by sequential degradation of its C-terminal amino acids, produced by the trypsin digestion, are the peaks that give an intensity in anionic species-based molecular weight measurement relatively larger than that in cationic species-based molecular weight measurement;

measuring the decrease in molecular weight associated with the sequential degradation of C-terminal amino acids, based on a series of peaks giving a relatively larger intensity in the anionic species-based molecular weight measurement.

(2) The method above, wherein the symmetric anhydride of an alkanoic acid of 2 to 4 carbon atoms is used as the alkanoic anhydride.

(3) The method above, wherein the symmetric anhydride of a straight-chain alkanoic acid of 2 to 4 carbon atoms is used as the symmetric anhydride of an alkanoic acid of 2 to 4 carbon atoms.

(4) The method above, wherein the acetic anhydride is used as the alkanoic anhydride.

(5) The method above, wherein, when the processing using the alkanoic anhydride is performed, the dry atmosphere is the state where moisture and also oxygen are removed.

(6) The method above, wherein the dry atmosphere is formed in an air-tight container by vacuum evacuation of the internal atmosphere.

(7) The method above, wherein the temperature when the processing using the alkanoic anhydride is performed, is selected in the range of 50° C. or higher and 80° C. or lower.

(8) A method of analyzing the C-terminal amino acid sequence of an analyte peptide, including;

preparing a mixture containing a series of reaction products obtained by sequential degradation of its C-terminal amino acids from the analyte peptide by chemical means;

analyzing the difference in molecular weight between the series of reaction products and the original peptide by mass spectrometry and measuring the decrease in molecular weight associated with the sequential degradation of C-terminal amino acids; and specifying a series of amino acids degraded sequentially based on the decrease in molecular weight of the series of reaction products and obtaining information on the C-terminal amino acid sequence by arranging them in order from the C-terminal, wherein the degrading the C-terminal amino acids sequentially at least includes:

dehydrating a gel carrier containing an analyte peptide sample previously isolated by gel electrophoresis and retained in the gel carrier by diluting and removing the water solvent impregnated in the gel carrier by using a polar aprotic solvent that does no dissolve the gel substance and has affinity with water;

allowing an alkanoic anhydride to act on the analyte peptide sample retained in the gel carrier after the dehydration, by immersing the gel carrier in an alkanoic anhydride solution containing the alkanoic anhydride dissolved in a dipolar aprotic solvent that can penetrate into the gel substance and make the gel into the swollen state at a temperature selected in the range of 50° C. or higher and 100° C. or lower;

N-acylating the analyte peptide N-terminal amino group and the side chain amino groups on the lysine-residue possibly contained in the peptide previously with the acyl group derived from the alkanoic acid constituting the alkanoic anhydride;

degrading of the C-terminal amino acids sequentially at the C-terminal of the peptide, via the 5-oxazolone structure represented by General Formula (III) above, along with cleavage of the 5-oxazolone ring; and terminating the degradation reaction and deleting the reaction reagents by diluting and removing the mixed solution used for the sequential reaction of degrading C-terminal amino acids by using a polar aprotic solvent that does not dissolve the gel substance and has affinity with the alkanoic anhydride and the dipolar aprotic solvent;

and additionally an additional hydrolytic step of hydrolyzing the mixture containing the series of reaction products obtained in the sequential degradation reaction of C-terminal amino acids while the mixture is retained in gel carrier by immersing the gel carrier in an aqueous solution containing a basic nitrogen-containing aromatic ring compound or a tertiary amine compound and thus, allowing the water molecule to act on the reaction product peptide in the presence of the basic nitrogen-containing organic compound, the measuring the decrease in molecular weight associated with the sequential degradation of C-terminal amino acids includes: fragmenting the peptide having the N-terminal amino group of the peptide chain and the side-chain amino groups of lysine residues possibly contained in the peptide chain, by the selective cleavage of the C-terminal-sided peptide bonds of arginine residues present in the peptide chain due to specific digestion of the peptide chain protected by N-acylation by trypsin enzyme, while allowing trypsin dissolved in a buffer solution to digest the mixture containing a series of reaction products re-anhydrated and hydrolyzed with retained in the gel carrier;

recovering the trypsin-digested peptide fragments by eluting the peptide fragments from the gel carrier into the buffer solution, desalting the buffer solution, and removing the buffer solution components; and then performing molecular weight measurement based on the cationic species and molecular weight measurement based on anionic species generated in the ionization processing on the dry mixture containing the recovered trypsin-digested peptide fragments by using a MALDI-TOF-MS method;

among the corresponding ionic species observed both in the cationic species-based and anionic species-based molecular weight measurement, assuming that the peaks of the peptide fragments having an arginine residue at the C-terminal produced by the trypsin digestion are the peaks that give an intensity in the cationic species-based molecular weight measurement relatively larger than that in anionic species-based molecular weight measurement and that the peaks of the C terminal peptide fragments derived from original peptide and those of a series of reaction products obtained by sequential degradation of its C-terminal amino acids produced by the trypsin digestion are the peaks that give an intensity in anionic species-based molecular weight measurement relatively larger than that in cationic species-based molecular weight measurement;

measuring the decrease in molecular weight associated with the sequential degradation of C-terminal amino acids, based on the series of peaks having a relatively larger intensity in the anionic species-based molecular weight measurement.

(9) The method above, wherein the symmetric anhydride of an alkanoic acid of 2 to 4 carbon atoms is used as the alkanoic anhydride.

(10) The method above, wherein the symmetric anhydride of a straight-chain alkanoic acid of 2 to 4 carbon atoms is used as the symmetric anhydride of an alkanoic acid of 2 to 4 carbon atoms.

(11) The method above, wherein acetic anhydride is used as the alkanoic anhydride.

EXAMPLES

Hereinafter, the present invention will be described more specifically with reference to Examples, but it should be understood that the invention is not limited to the specific configurations in the following Examples.

Example 1

In the present Example, the C-terminal amino acid sequence of a protein retained in gel was analyzed. The protein used was an horse myoglobin (sequence No. 1). The horse myoglobin is a hem protein consisting of 153 amino acids. The analyte sample myoglobin was first purified into a single spot by SDS-PAGE. The C-terminal amino acid sequence thereof was then determined according to the method described in the first embodiment (FIGS. 4 and 5) and also to that in the second embodiment (FIG. 6).

(Isolation by Gel Electrophoresis)

First, a peptide solution containing only a globin peptide-chain region at a concentration of 0.2 µg/µL was prepared from a commercial horse myoglobin authentic preparation. The peptide solution was spotted on a polyacrylamide gel at a gel concentration of 12.5 mass % and subjected to electrophoresis. The band of the desirable globin peptide chain was specified by CBB staining. The gel corresponding to the stained band was cut off, and used in analysis of C-terminal amino acid sequence.

(Dehydration of Gel)

The separated gel was cut into cubes of 1 mm cubic. The gel cubes were placed in an air-tight tube and stirred in 1 mL of acetonitrile added therein for 15 minutes. Then, acetonitrile was discarded, additional 1 mL of acetonitrile was added; and the mixture was stirred additionally for 15 minutes. For dehydration of the gel, the extraction of the water impregnated in the gel was repeated a total of three times. The gel volume decreases with progress of dehydration.

(Acetylation and C-Terminal Amino Acid-Cleavage Reactions)

Then, 1 mL of a formamide solution containing acetic anhydride at 30 vol % concentration was added to the dehydrated gel slices placed in a tube. The tube was sealed and heated to 50° C. and held at the condition for 110 hours while the mixture was stirred at dry atmosphere.

The gel once contracted in volume reswelled its volume by invasion of formamide, while it is held under heat. The solute acetic anhydride reacts with the globin peptide chain held in the re-swollen gel at the heated temperature, causing progress of selective acetylation of the peptide N-terminal amino group. In addition, N-acetylation of the ε-amino groups of lysine residues contained in the peptide chain and O-acetylation of the hydroxyl groups present in the serine and threonine residues and also of the phenolic hydroxyl groups of the tyrosine residues (—NH—CH(CH$_2$—C$_6$H$_4$—OH)—CO—) proceed at the same time.

Further, when acetic anhydride is allowed to act on the C-terminal of the peptide chain retained in the re-swollen gel at the heated temperature, selective degradation reaction of the C-terminal amino acids of the peptide chain proceeds together with acetylation. Specifically, it seems that sequential degradation reaction of the C-terminal amino acids of peptide chain occurs at the C-terminal of the peptide, via the 5-oxazolone ring formation, in the reaction pathways represented by Formulae (Ia), (Ib) and (II').

The sequential degradation reaction of C-terminal amino acid leaves a mixture of a series of reaction products in which C-terminal amino acids are deleted stepwise and the original peptide protected by acetylation in the gel.

(Posttreatment)

Then, 1 mL of an aqueous solution containing 10 vol % DMAE was injected into the container containing the gel slices, and the mixture was stirred for 20 minutes. Then, the aqueous DMAE solution was discarded. 1 mL of a new aqueous DMAE solution was injected; the mixture was stirred additionally for 20 minutes; and the aqueous DMAE solution was discarded. The operation of injecting the aqueous DMAE solution, stirring and removal of the solution was repeated three times. An additional aqueous DMAE solution was injected; the mixture was stirred for 20 minutes, and the container was sealed tightly and heated to a temperature of 60° C. and kept at the same temperature for 1 hour while the mixture was stirred. Hydrolysis of the peptides retained in the re-swollen gel progresses while water molecules act on the peptides in the presence of a basic nitrogen-containing organic compound at the heated temperature.

The aqueous solution remaining in the container was removed after the posttreatment step, 1 mL of acetonitrile was added to the container, and the mixture was stirred for 15 minutes. After disposal of acetonitrile, an additional 1 mL of acetonitrile was injected; and the mixture was stirred additionally for 15 minutes. Extraction of the aqueous solution impregnated in the gel was repeated a total of three times, allowing dehydration of the re-swollen gel. The gel volume contracted during dehydration.

(Peptide Fragmentation by Trypsin Digestion)

The globin peptide chain in horse myoglobin consists of 153 amino acids (sequence No. 1). The peptide chain was fragmented then by trypsin digestion, to give fragments having a molecular weight in a range more suitable for analysis by MALDI-TOF-MS.

After posttreatment, the peptide chains were fragmented while held in the gel, by adding an aqueous trypsin solution into a container containing the dehydrated gel slices. An aqueous trypsin solution containing trypsin at a concentration of 0.067 μg/μL in ammonium bicarbonate buffer solution (pH 8) was used at the time. The enzyme reaction was continued for 4 hours, while the gel cubes were stirred at 37° C. The dehydrated gel then re-swelled rapidly by invasion of the aqueous solution. Reaction of trypsin with the peptides retained in the re-swollen gel together with the buffer solution leads to enzyme digestion specific to trypsin.

Protecting groups on the peptide N-terminal amino group and the ε-amino groups of lysine residues by N-acetylation were preserved even after deprotection in the posttreatment step and the C-terminal-sided peptide bonds of N-acetylated lysine residues are not cleaved, while the C-terminal-sided peptide bonds of arginine residues are cleaved by trypsin digestion.

The amino acid sequence of the globin peptide chain in horse myoglobin is already known, and, as shown in FIG. 7, along with cleavage of the C-terminal-sided peptide bonds of arginine residue cleavages, the original peptide chain having 153 amino acids is cleaved into fragments having the sequence of 1 to 31 (sequence No. 2), 32 to 139 (sequence No. 3), and 140 to 153 (sequence No. 4) by trypsin digestion.

When the globin peptide chain is fragmented by trypsin digestion, the peptide fragments elutes more easily from the gel into the trypsin solution in the container. In the trypsin digestion step, C-terminal fragments containing the partial amino acid sequence of 140 to 153 amino acids and also the C-terminal fragments derived from the series of reaction products produced by the sequential degradation of C-terminal amino acids described above elute into the trypsin solution in the container. The digestion allows conversion of the C-terminal region of a peptide having a long amino-acid length chain into peptide fragments having a molecular weight in a range favorable for mass spectrometric analysis, and also, elution and recovery of the peptide fragments from the gel at high yield.

The eluted peptide fragments are recovered, after the trypsin digestion step. The solution containing the recovered peptide fragment mixture was desalted and dried under vacuum.

(Mass Spectrometry and Analysis of C-Terminal Amino Acid Sequence)

The series of processings above gave a mixture of the C-terminal-sided fragments and the C-terminal amino acid-lacking fragments of the globin peptide chain. The molecular weight of peptide fragments in the mixture was measured by mass spectrometry. The mass and relative intensity of the peaks of main ion species reflecting the molecular weight of respective peptide fragments were measured and compared by using a MALDI-TOF-MS device.

In measurement with the MALDI-TOF-MS device, both measurements in the so-called negative mode in which negatively charged ionic species are introduced into the detector after separation of ionic species and in the so-called positive mode in which positively charged ionic species are introduced into the detector are performed. Thus, the main ion species reflecting the molecular weight of respective peptide fragments include cationic species and anionic species. In the present Example, a spectrum corresponding to cationic species having an added proton was obtained in the positive-mode measurement. While in the negative-mode measurement, a spectrum corresponding to anionic species having the proton eliminated was obtained.

When the results in positive-mode measurement and negative-mode measurement were compared, two main peaks corresponding to the trypsin-digestion fragments derived from the horse myoglobin globin peptide chain, respectively having an amino acid sequence containing the region of 1 to 31 and an amino acid sequence containing the region of 140 to 153 were observed. The peak having an intensity relatively larger in the positive-mode measurement were considered to correspond to the N-terminal-sided peptide fragment of the amino acid sequence in the region of 1 to 31 having an arginine residue at the C-terminal. On the other hand, the peak having intensity relatively larger in the negative-mode measurement was determined to correspond to the C-terminal-sided peptide fragment of the amino acid sequence in the region of 140 to 153 containing no arginine residue.

In addition, a peptide fragment corresponding to the amino acid sequence in the region of 78 to 102 in the amino acid sequence in the region of 32 to 139, which was generated by cleavage of a lysine residue from which the N-acetyl group is eliminated, was also found. The peptide fragment also showed intensity relatively larger in the positive-mode measurement. In addition, peptide fragments generated by autodigestion of trypsin were also found, which showed intensity relatively larger in the positive-mode measurement.

Thus in the present Example, it was possible to identify the C-terminal peptide fragments and the C-terminal amino acid-deleted peptides produced by sequential degradation easily by comparing the results obtained in positive-mode measurement and negative-mode measurement.

Figure 8:
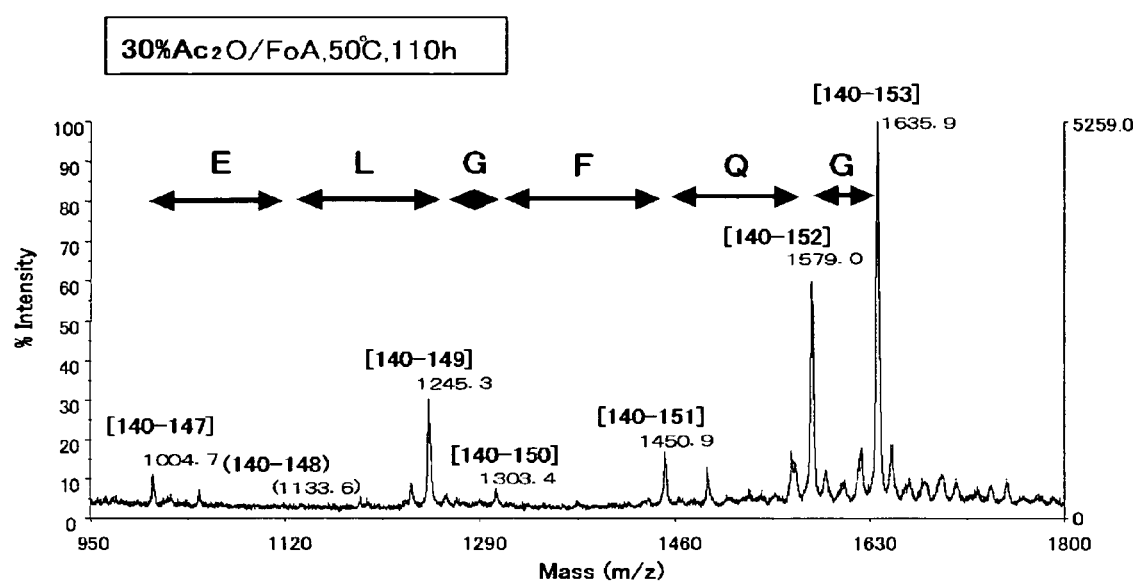
FIG. 8 is a graph showing mass spectrum of the globin peptide chain according to the Example.

FIG. 8 is a graph showing mass spectrum obtained in the negative-mode measurement. In FIG. 8, the C-terminal-sided peptide fragments from the amino acid sequence in the region of 140 to 153 and a series of C-terminal-sided peptide fragments derived from the reaction products by sequential degradation of C-terminal amino acids are measured to be relatively larger. Table 1 shows the difference in mass between the respective measured peaks and the peak derived from the C-terminal-sided peptide fragment of the original globin peptide chain. It also shows the amino acids deleted from the C-terminal and the sequences of the C-terminal-deleted peptides identified from these differences.

TABLE 1

| m/z | Δm | ASSIGNMENT | CORRESPONDING PEPTIDE STRUCTURE |
|---|---|---|---|
| 1635.9 | — | — | NDIAAK(Ac)YK(Ac)ELGFQG |
| 1579.0 | 56.9 | -Gly | NDIAAK(Ac)YK(Ac)ELGFQ |
| 1450.9 | 128.1 | -Gln-Gly | NDIAAK(Ac)YK(Ac)ELGF |
| 1303.4 | 147.5 | -Phe-Gln-Gly | NDIAAK(Ac)YK(Ac)ELG |
| 1245.3 | 58.1 | -Gly-Phe-Gln-Gly | NDIAAK(Ac)YK(Ac)EL |
| 1133.6 | 111.7 | -Leu-Gly-Phe-Gln-Gly | NDIAAK(Ac)YK(Ac)E |
| 1004.7 | 128.9 | -Glu-Leu-Gly-Phe-Gln-Gly | NDIAAK(Ac)YK(Ac) |

As apparent from the results in FIG. 8 and Table 1, there were observed six peaks corresponding to the reaction products in which six amino acids, that is, glycine, glutamine, phenylalanine, glycine, leucine, and glutamic acid, are degraded sequentially by the sequential degradation using acetic anhydride according to the present Example. Thus, it was found that the peptide isolated as a band in the gel slice was the globin peptide chain, and that the sequential degradation of C-terminal amino acids could be performed while the peptide was retained in the gel.

It is thus obvious that it was possible to perform measurement at high accuracy and reliability by using the method described in the first embodiment even when the C-terminal amino acids of the analyte peptide chain was degraded sequentially while retained in the gel.

It was also possible to differentiate the desirable C-terminal-sided peptide fragments from the accompanying series of C-terminal sided peptide fragments previously subjected to sequential degradation of C-terminal amino acids easily, because the peptide fragments which is trypsin-digested at lysine residues did not have a molecular weight in the range for use in the analysis of C-terminal amino acid sequence.

The globin peptide chain region of horse myoglobin used in the present Example has no cysteine residue, unlike human myoglobin; but peptides containing cysteine residues inside such as human myoglobin may be processed previously, for example, by adding a reducing agent such as 2-sulfanylethanol or DTT, for prevention of the —S—S— bond formation by oxidation of the sulfanyl groups (—SH) of the cysteine residues. In some cases, the sulfanyl groups may be protected, for example, by carboxymethylation after reduction of the cysteine residues.

Example 2

In the present Example, acceleration of the sequential degradation reaction in Example 1 by adding pyridine to the system therein was evaluated. The sample used was the globin peptide chain of horse myoglobin. The gel was immersed in an aqueous solution containing 1 vol % pyridine before dehydration of the gel. The mixture in tube was stirred during immersion. After immersion for 20 minutes, the aqueous pyridine solution was exchanged, and the immersion was continued. The sample after immersion was processed according to the method described in the Example above. However, the sequential C-terminal degradation was performed at 60° C. for 16 hours.

Figure 9:
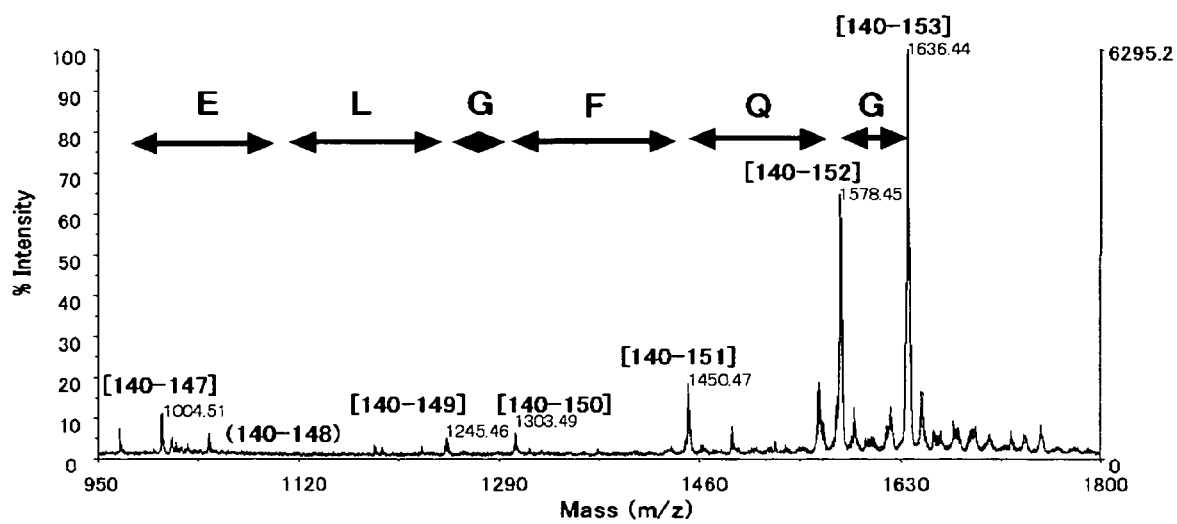
FIG. 9 is a graph showing mass spectrum of the globin peptide chain according to the Example.

The sample obtained was analyzed by mass spectrometry, similarly to the Example above. FIG. 9 is a graph showing mass spectrum obtained in the negative-mode measurement. Table 2 shows the difference in mass between the respective measured peaks and the peak derived from the C-terminal-sided peptide fragment of the original globin peptide chain. It also shows the amino acids deleted from the C-terminal and the sequences of the C-terminal-deleted peptides identified from these differences.

TABLE 2

| m/z | Δm | ASSIGNMENT | CORRESPONDING PEPTIDE STRUCTURE |
|---|---|---|---|
| 1636.44 | — | — | NDIAAK(Ac)YK(Ac)ELGFQG |
| 1578.45 | 57.99 | -Gly | NDIAAK(Ac)YK(Ac)ELGFQ |
| 1450.47 | 127.98 | -Gln-Gly | NDIAAK(Ac)YK(Ac)ELGF |
| 1303.49 | 146.98 | -Phe-Gln-Gly | NDIAAK(Ac)YK(Ac)ELG |
| 1245.46 | 58.03 | -Gly-Phe-Gln-Gly | NDIAAK(Ac)YK(Ac)EL |
| 1134.60 | 113.00 | -Leu-Gly-Phe-Gln-Gly | NDIAAK(Ac)YK(Ac)E |
| 1004.51 | 130.00 | -Glu-Leu-Gly-Phe-Gln-Gly | NDIAAK(Ac)YK(Ac) |

Figure 10:
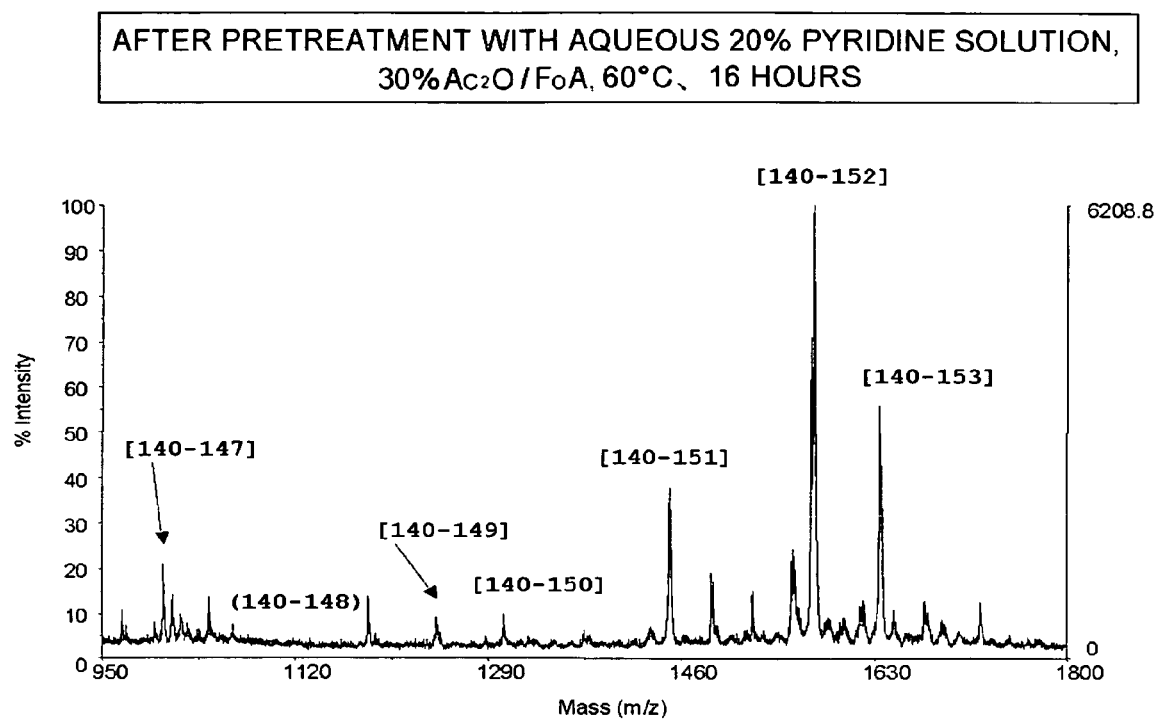
FIG. 10 is a graph showing mass spectrum of the globin peptide chain according to the Example.

Further, a case when the gel was immersed in an aqueous vol % pyridine solution for 2 hours and the sequential C-terminal degradation was performed at 60° C. for 16 hours was also evaluated. Other conditions are the same as those in the Example above. FIG. 10 is a graph showing mass spectrum obtained in the negative-mode measurement.

Figure 11:
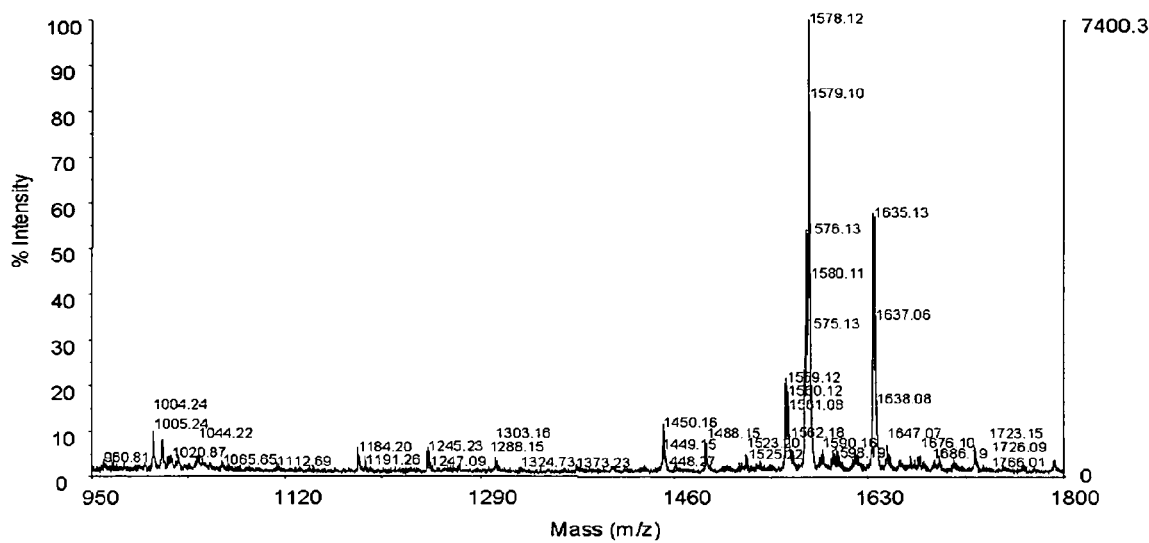
FIG. 11 is a graph showing mass spectrum of the globin peptide chain according to the Example.

Further, a case when the gel was immersed in an aqueous vol % pyridine solution three times and the sequential C-terminal degradation was performed at 60° C. for 1 hour was also evaluated. Other conditions are the same as those in the Example above. FIG. 11 is a graph showing mass spectrum obtained in the negative-mode measurement.

As apparent from the results in FIGS. 9, 10, and 11 and Table 2, when the gel was processed to contain pyridine by using the method described in the second embodiment, there were observed six peaks corresponding to the reaction products in which six amino acids, that is, glycine, glutamine, phenylalanine, glycine, leucine, and glutamic acid are degraded sequentially from the C-terminal.

It was also possible to shorten the sequential degradation reaction period markedly by processing with pyridine. It seems that the reaction is accelerated in each reaction process of the sequential degradation by catalysis of acetic anhydride, which functions as a proton donor in formamide being the amphoteric solvent.

In addition, comparison of the results in FIGS. 10 and 11 with those in FIG. 9 reveals that the peaks of C-terminal amino acid-deleted peptides have an intensity significantly larger than that of the C-terminal-sided fragment peptides of the original peptide when an aqueous 20 vol % pyridine solution was used. Thus, use of the aqueous 20 vol % pyridine solution is effective in further shortening the sequential degradation reaction period. As shown in FIG. 11, it was possible to decompose the peptides in the gel stably in one hour under a relatively mild heating condition at 60° C.

Example 3

In the present Example, enhancement of the mass spectrometry signal by using the crosslinking agent described above in the third embodiment was evaluated. The crosslinking agent used was glutaraldehyde. The analyte protein used was soybean trypsin inhibitor.

(Preparation of Glutaraldehyde Solution)

An aqueous solution containing 1.25 pmol/μL glutaraldehyde, 1.13 M NaAc, 30 v/v % ethanol, and 0.2 w/v % $Na_2S_2O_3$ was prepared. However, glutaraldehyde was added immediately before use. A gel containing the protein was immersed in the glutaraldehyde solution allowing the reaction to proceed for 1 hour at room temperature. The gel was then washed with aqueous solution and used in the sequential degradation reaction according to the method described in Example 1.

(Mass Spectrometry)

Figure 12:
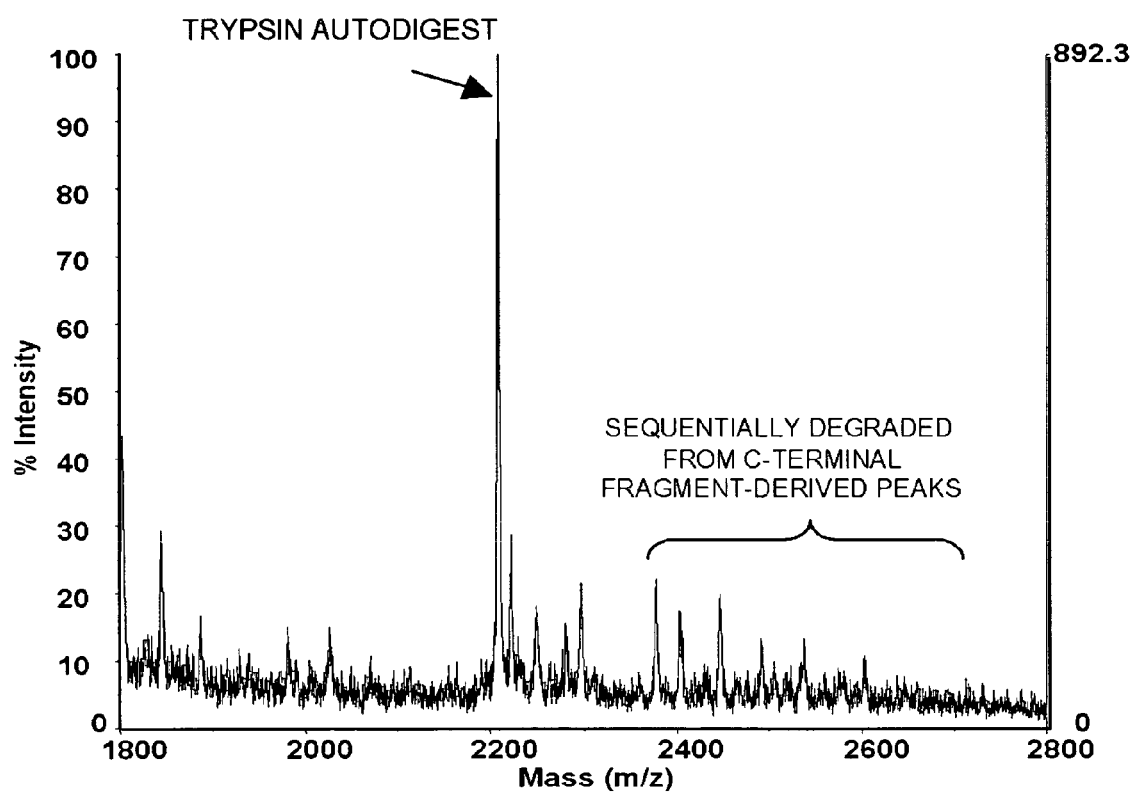
FIG. 12 is a graph showing mass spectrum of trypsin inhibitor according to the Example.
Figure 13:
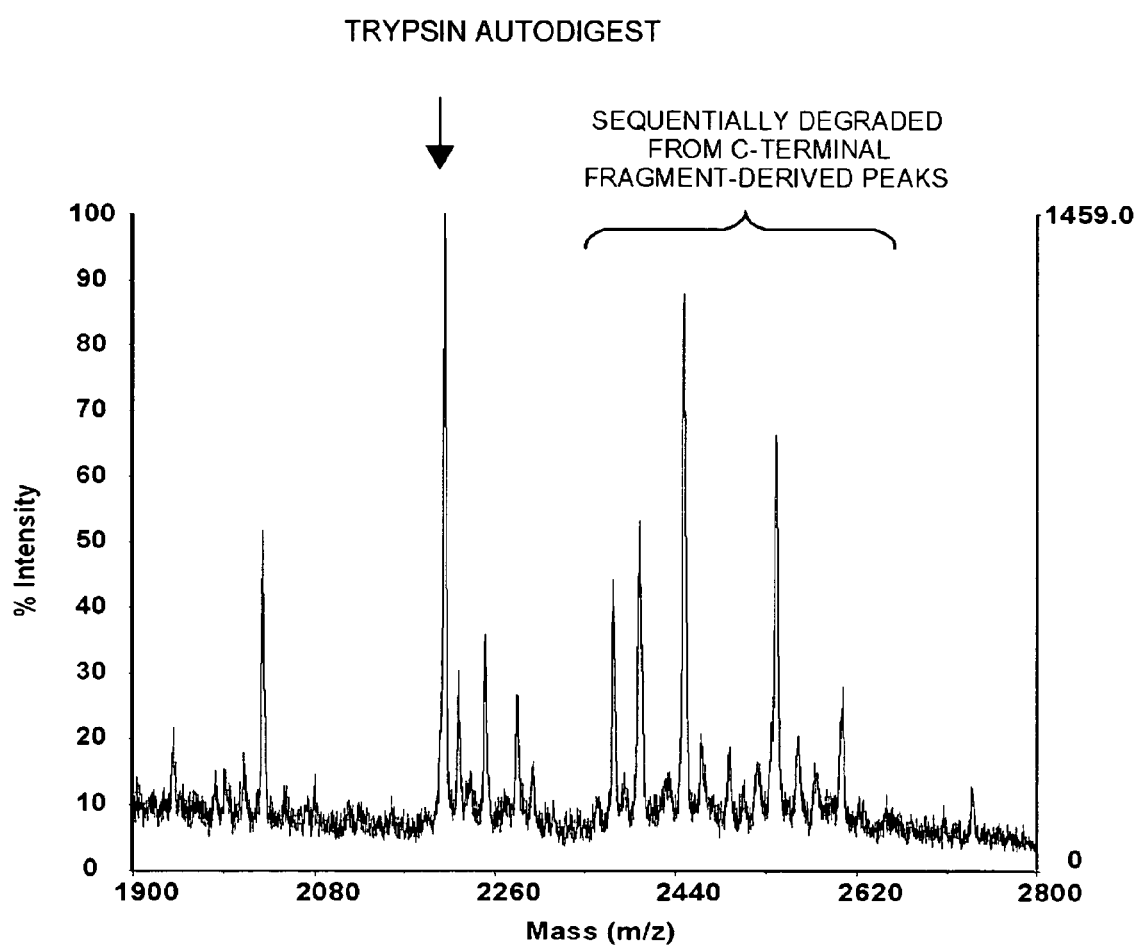
FIG. 13 is a graph showing mass spectrum of the trypsin inhibitor according to the Example.

The improvement in recovery rate by glutaraldehyde was compared between when the protein is immobilized and not. FIG. 12 is a graph showing mass spectrum of a sample obtained when the sequential degradation was performed without immobilization with glutaraldehyde. In FIG. 12, 8 μg of trypsin inhibitor was used as the sample. Alternatively, FIG. 13 is a graph showing mass spectrum of a sample obtained when the sequential degradation was performed after immobilization by using the aqueous glutaraldehyde solution described above. In FIG. 13, 5 μg of trypsin inhibitor was used as the sample.

As obvious in FIG. 12, the sample-derived peaks are relatively weaker in intensity than the peaks of the autodigestion products of trypsin. In contrast in FIG. 13, the sample-derived peaks have an intensity relatively stronger than that of the trypsin autodigests. The results indicate that glutaraldehyde immobilization before sequential C-terminal degradation improves the recovery rate of the peptide fragments of C-terminal-deleted peptides. In FIG. 13, there were observed signals of the sequentially-degraded products up to four amino acid residues form the C-terminal.

As described above, it was possible to obtain C-terminal fragments degraded sequentially, by performing crosslinking reaction of the analyte protein under the condition described above by using glutaraldehyde as a crosslinking agent.

The invention claimed is:

1. A method of analyzing the C-terminal amino acid sequence of a peptide, comprising:
   obtaining C-terminal-deleted peptides lacking amino acid residues from said C-terminal by degrading the amino acids from said peptide C-terminal sequentially;
   measuring the molecular weight of said C-terminal-deleted peptides; and
   determining the decrease in molecular weight associated with said sequential degradation from the difference between the molecular weight obtained in said measuring the molecular weight of the C-terminal-deleted peptides and the molecular weight of said peptide, and analyzing said C-terminal amino acid sequence based on the decrease in said molecular weight, wherein said C-terminal amino acids are degraded by making said peptide substantially bring into contact with an alkanoic anhydride in said obtaining C-terminal-deleted peptides, wherein said obtaining the C-terminal-deleted peptides is carried out in a system containing a basic nitrogen-containing aromatic ring compound, and wherein said C-terminal amino acids are degraded with alkanoic anhydride, without a perfluoroalkanoic acid or the anhydride thereof, in said step of obtaining C-terminal-deleted peptides.

2. The method of analyzing the C-terminal amino acid sequence of the peptide according to claim 1, further comprising measuring the molecular weight of said peptide, wherein said analyzing the amino acid sequence enables the decrease in molecular weight associated with the sequential degradation to be determined from the difference between the molecular weight obtained in said measuring the molecular weight of the peptide and the molecular weight obtained in said measuring the molecular weight of C-terminal-deleted peptides.

3. The method of analyzing the C-terminal amino acid sequence of the peptide according to claim 1, further comprising allowing water molecules to act on said C-terminal-deleted peptides after said obtaining the C-terminal-deleted peptides and before said measuring the molecular weight of the C-terminal-deleted peptides.

4. The method of analyzing the C-terminal amino acid sequence of the peptide according to claim 3, wherein said allowing water molecules to act includes bringing said C-terminal-deleted peptides into contact with an aqueous solution containing a basic nitrogen-containing compound or a tertiary amine.

5. A method of analyzing the C-terminal amino acid sequence of a peptide, comprising:

obtaining C-terminal-deleted peptides lacking amino acid residues from said C-terminal by degrading the amino acids from said C-terminal of said peptide sequentially;

obtaining C-terminal-deleted peptide-derived peptide fragments by cleaving said C-terminal-deleted peptides at predetermined positions;

measuring the molecular weight of said C-terminal-deleted peptide-derived peptide fragments;

determining the decrease in molecular weight associated with said sequential degradation from the difference between the molecular weight obtained in said measuring the molecular weight of C-terminal-deleted peptide-derived peptide fragments and the molecular weight of the peptide fragments obtainable from said peptide and analyzing said C-terminal amino acid sequence based on said decrease in molecular weight, wherein said C-terminal amino acids are degraded by making said peptide substantially bring into contact with an alkanoic anhydride in said obtaining C-terminal-deleted peptides, wherein said obtaining the C-terminal-deleted peptide is carried out in a system containing a basic nitrogen-containing aromatic ring compound, and wherein said C-terminal amino acids are degraded with alkanoic anhydride, without a perfluoroalkanoic acid or the anhydride thereof, in said step of obtaining C-terminal-deleted peptides.

6. The method of analyzing the C-terminal amino acid sequence of the peptide according to claim 5, further comprising:

obtaining peptide-derived peptide fragments by cleaving said peptide at said predetermined positions; and measuring the molecular weight of said peptide-derived peptide fragments, wherein the decrease in molecular weight associated with said sequential degradation is determined from the difference between the molecular weight obtained in said measuring the molecular weight of the peptide-derived peptide fragments and the molecular weight obtained in said measuring the molecular weight of C-terminal-deleted peptide-derived peptide fragments.

7. The method of analyzing the C-terminal amino acid sequence of the peptide according to claim 5, wherein said obtaining the C-terminal-deleted peptides includes protecting particular amino acid residues in said peptide and thus eliminating the susceptibility of said particular amino acid residues to said cleavage in said obtaining the C-terminal-deleted peptide-derived peptide fragments.

8. The method of analyzing the C-terminal amino acid sequence of the peptide according to claim 7, wherein said obtaining the C-terminal-deleted peptide-derived peptide fragments includes treating said C-terminal-deleted peptides with a protease.

9. The method of analyzing the C-terminal amino acid sequence of the peptide according to claim 8, wherein said protease is trypsin, and said eliminating the susceptibility of the particular amino acid residues includes N-acylating said peptide.

10. The method of analyzing the C-terminal amino acid sequence of the peptide according to any one of claims 7 to 9, wherein said protection is O- and N-acylation of said peptide and the protecting groups by O-acylation are deprotected after said obtaining the C-terminal-deleted peptide and before said obtaining the C-terminal-deleted peptide-derived peptide fragments.

11. The method of analyzing the C-terminal amino acid sequence of the peptide according to claim 5, wherein said measuring the molecular weight of C-terminal-deleted peptide-derived peptide fragments includes performing mass spectrometric measurement based on cationic and anionic species; and said analyzing the amino acid sequence from the C-terminal includes identifying said C-terminal-deleted peptide-derived peptide fragments associated with said C-terminal of said peptide by comparing the mass spectrometric results based on cationic species and the mass spectrometric results based on anionic species.

12. The method of analyzing the C-terminal amino acid sequence of the peptide according to claim 5, further comprising allowing water molecules to act on said C-terminal-deleted peptides after said obtaining the C-terminal-deleted peptides and before said obtaining the C-terminal-deleted peptide-derived peptide fragments.

13. The method of analyzing the C-terminal amino acid sequence of the peptide according to claim 12, wherein said allowing water molecules to act includes bringing said C-terminal-deleted peptides into contact with an aqueous solution containing a basic nitrogen-containing aromatic ring compound or a tertiary amine.

14. The method of analyzing the C-terminal amino acid sequence of the peptide according to claim 5, wherein said obtaining the C-terminal-deleted peptides is carried out while said peptide is retained in a gel.

15. The method of analyzing the C-terminal amino acid sequence of the peptide according to claim 1, wherein said obtaining prior to said measuring the molecular weight of the C-terminal-deleted peptides are performed in a gel.

16. The method of analyzing the C-terminal amino acid sequence of the peptide according to claim 5,
wherein said obtainings prior to said measuring the molecular weight of C-terminal-deleted peptide-derived peptide fragments are performed in a gel.

17. The method of analyzing the C-terminal amino acid sequence of the peptide according to claim 14, further comprising crosslinking said peptide before said obtaining the C-terminal-deleted peptides.

18. The method of analyzing the C-terminal amino acid sequence of the peptide according to claim 14, further comprising isolating said peptide from the peptide-containing mixture by polyacrylamide gel electrophoresis before said obtaining the C-terminal-deleted peptides,
wherein said obtaining the C-terminal-deleted peptides is performed while said isolated peptide is retained in said gel used in said polyacrylamide gel electrophoresis.

19. The method of analyzing the C-terminal amino acid sequence of the peptide according to claim 14,
wherein said obtaining the C-terminal-deleted peptides includes immersing said gel in a solution of an alkanoic anhydride in a dipolar aprotic solvent.

20. The method of analyzing the C-terminal amino acid sequence of the peptide according to claim 1,
wherein said basic nitrogen-containing aromatic ring compound is a pyridine base or the derivative of the pyridine base.

21. The method of analyzing the C-terminal amino acid sequence of the peptide according to claim 1,
wherein said alkanoic anhydride is the symmetric anhydride of an alkanoic acid of 2 or more and 6 or less carbon atoms.

22. The method of analyzing the C-terminal amino acid sequence of the peptide according to claim 1,
wherein said alkanoic anhydride is the symmetric anhydride of a straight-chain alkanoic acid of 2 or more and 6 or less carbon atoms.

* * * * *

SEQUENCE LISTING

```
<160> NUMBER OF SEQ ID NOS: 4

<210> SEQ ID NO 1
<211> LENGTH: 153
<212> TYPE: PRT
<213> ORGANISM: Equus caballus

<400> SEQUENCE: 1

Gly Leu Ser Asp Gly Glu Trp Gln Gln Val Leu Asn Val Trp Gly Lys
1               5                   10                  15

Val Glu Ala Asp Ile Ala Gly His Gly Gln Glu Val Leu Ile Arg Leu
            20                  25                  30

Phe Thr Gly His Pro Glu Thr Leu Glu Lys Phe Asp Lys Phe Lys His
        35                  40                  45

Leu Lys Thr Glu Ala Glu Met Lys Ala Ser Glu Asp Leu Lys Lys His
    50                  55                  60

Gly Thr Val Val Leu Thr Ala Leu Gly Gly Ile Leu Lys Lys Lys Gly
65                  70                  75                  80

His His Glu Ala Glu Leu Lys Pro Leu Ala Gln Ser His Ala Thr Lys
            85                  90                  95
```

```
His Lys Ile Pro Ile Lys Tyr Leu Glu Phe Ile Ser Asp Ala Ile Ile
100             105                 110

His Val Leu His Ser Lys His Pro Gly Asn Phe Gly Ala Asp Ala Gln
115             120                 125

Gly Ala Met Thr Lys Ala Leu Glu Leu Phe Arg Asn Asp Ile Ala Ala
130             135                 140

Lys Tyr Lys Glu Leu Gly Phe Gln Gly
145             150

<210> SEQ ID NO 2
<211> LENGTH: 31
<212> TYPE: PRT
<213> ORGANISM: Equus caballus

<400> SEQUENCE: 2

Gly Leu Ser Asp Gly Glu Trp Gln Gln Val Leu Asn Val Trp Gly Lys
1               5                   10                  15

Val Glu Ala Asp Ile Ala Gly His Gly Gln Glu Val Leu Ile Arg
20                  25                  30

<210> SEQ ID NO 3
<211> LENGTH: 108
<212> TYPE: PRT
<213> ORGANISM: Equus caballus

<400> SEQUENCE: 3

Leu Phe Thr Gly His Pro Glu Thr Leu Glu Lys Phe Asp Lys Phe Lys
1               5                   10                  15

His Leu Lys Thr Glu Ala Glu Met Lys Ala Ser Glu Asp Leu Lys Lys
20                  25                  30

His Gly Thr Val Val Leu Thr Ala Leu Gly Gly Ile Leu Lys Lys Lys
35                  40                  45

Gly His His Glu Ala Glu Leu Lys Pro Leu Ala Gln Ser His Ala Thr
50                  55                  60

Lys His Lys Ile Pro Ile Lys Tyr Leu Glu Phe Ile Ser Asp Ala Ile
65                  70                  75                  80

Ile His Val Leu His Ser Lys His Pro Gly Asn Phe Gly Ala Asp Ala
85                  90                  95

Gln Gly Ala Met Thr Lys Ala Leu Glu Leu Phe Arg
100             105

<210> SEQ ID NO 4
<211> LENGTH: 14
<212> TYPE: PRT
<213> ORGANISM: Equus caballus

<400> SEQUENCE: 4

Asn Asp Ile Ala Ala Lys Tyr Lys Glu Leu Gly Phe Gln Gly
1               5                   10
```